US006316195B1

(12) United States Patent
Frederick et al.

(10) Patent No.: US 6,316,195 B1
(45) Date of Patent: Nov. 13, 2001

(54) METHOD FOR DIFFERENTIATING BETWEEN THE CASUAL AGENTS OF KARNAL BUNT WHEAT FUNGUS AND RYEGRASS SMUT USING PCR

(75) Inventors: Reid D. Frederick, Ashburn, VA (US); Paul W. Tooley, Braddock Heights; Morris R. Bonde, Middletown, both of MD (US); David A. Knorr, San Leandro, CA (US); Gary L. Peterson, Frederick; Norman W. Schaad, Myersville, both of MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/471,016

(22) Filed: Dec. 23, 1999

(51) Int. Cl.$^7$ ............... C07H 21/04; C12Q 1/68
(52) U.S. Cl. ............ 435/6; 435/91.1; 536/23.1; 536/24.32
(58) Field of Search ............ 435/6, 91.1; 536/23.1, 536/24.32

(56) References Cited

U.S. PATENT DOCUMENTS 5,811,240 * 9/1998 Ferreira et al. ............... 435/6

OTHER PUBLICATIONS

Smith et al., "Development of a PCR–Based Method for Identification of *Tilletia indica*, Causal Agent of Karnal Bunt of Wheat", *Phytopathology*, vol. 86(1), pp. 115–122, 1996.
Ferreira et al., "Isolation of a Species–Specific Mitochondrial DNA Sequence for Identification of *Tilletia indica*, the Karnal Bunt of Wheat Fungus", *Applied and Environmental Microbiology*, vol. 62(1), pp. 87–93, Jan. 1996.
Berthier–Schaad et al., "Rapid, Automated PCR–Based Technique for Identification of *Tilletia indica*", (Abstract) *Phytopathology*, Aug. 9–13, 1997.
Smith et al., "Development of a PCR–Based Assay to Identify *Tilletia indica*, Causal Agent of Karnal Bunt of Wheat", (Abstract) *Phytopathology*, vol. 84, p. 1152, 1994.
Bonde et al., *Plant Disease*, vol. 81(12), pp. 1370–1377, Dec. 1997.
Frederick et al "An improved PCR method utilizing TaqMan for the detection and differnetiation of Tilletia indica, the causal organism fo Karnal bun of wheat and a related ryegrass smut" Phytopathology, vol. 88, No. 9 Suppl, p. S29.*

* cited by examiner

*Primary Examiner*—Lisa B. Arthur
*Assistant Examiner*—Jeanine Goldberg
(74) *Attorney, Agent, or Firm*—M. Howard Silverstein; John D. Fado; Evelyn M. Rabin

(57) ABSTRACT

Karnal bunt of wheat is caused by *Tilletia indica* Mitra. Recently, teliospores morphologically resembling *T. indica* were isolated from bunted ryegrass seeds and wheat seed washes. Previously developed PCR assays failed to differentiate *T. indica* from the newly discovered ryegrass pathogen, *T. walkeri*. The nucleotide sequence of a 2.3-kb region of mitochondrial DNA, previously amplified by PCR only from *T. indica*, was determined for three isolates of *T. indica* and for three isolates of *T. walkeri*. There was greater than 99% identity within either the *T. indica* group or the *T. walkeri* group of isolates, whereas there was approximately 3% divergence between isolates of these two Tilletia species. Five sets of PCR primers were made specific to *T. indica*, and three sets were designed specifically for *T. walkeri* based upon nucleotide differences within the mtDNA region. In addition, a 212 bp amplicon was developed as a target sequence in a fluorogenic 5' nuclease PCR assay using the TaqMan system for the detection and discrimination of *T. indica* and *T. walkeri*.

19 Claims, 12 Drawing Sheets

|    |                                                                                      |     |
|----|--------------------------------------------------------------------------------------|-----|
|    | ────────Ti-1───────▶                                                                 |     |
| Ti | TGGCTGAGTCTGAGATGCAGAGCCTGCACTCCCGAAAACGTCGACGAGTTTGGCCGACGAAGCGTGTGCGACACCCGA        | 80  |
| Tw | TGGGCTGAGTCTGAGATGCAGAGCCTGCACTCCCGAAAACGTCGACGAGTTTGCCGACGAAGCGTGTGCGACACCCGA        | 80  |
| Ti | ATCCGTGGAAGAACAACGCTGAGTGATCCTAGCTGAGCTAACGCCGTCCTGGATTGTGCACTCTCGTCACCGCGTTGC        | 160 |
| Tw | ATCCGTGGAAGAACAACGCTGAGTGATCCTAGCTGAGCTAACGCCGTCCTGGATTGTGCACTCTCGTCACCGCGTTGC        | 160 |
| Ti | GCGCTTAGCGGTGAATGCTCCTGGAAGCCACAGAGCTATCAGCAAATGACTCGAA...CAGTTTTGTTCATCACACAAGA      | 237 |
| Tw | GCGCTTAGCGGTGAATGCTCCTGGAAGCCACAGAGCTATCAGCAAATGACTCGAACAAGCAGTTTGTTCATCACACAAGA      | 240 |
| Ti | CTCACTTGAGCGGCTCCGCTCGCCCTTCTTCTTCTGCAATAGTACCTGTGGCCTCCCCTAGGGAAGGGCTGCCAGGCTCCTTGG  | 317 |
| Tw | CTCACTTGAGCGGCTCCGCTCGCCCTTCTTCTTCTGCAATAGTACCTGTGGCCTCCCCTAGGGAAGGGCTGCCAGGCTCCTTGG  | 320 |
|    | ─────F3─────▶                                                                        |     |
| Ti | CTGGCACCAGAGTACAGCTGTGTCTTCCTGCCTCGTTTCACCAGAGACATGACTTTCATGATGCCTCGATACCAAC          | 397 |
| Tw | CTGGCACCAGAGTACAGCTGTGTCTTCCTGCCTCGTTTCACCAGAGACATGACTTTCATGATGCCTCTATACCGAC          | 400 |
| Ti | GTTGGTCTCGGCCAGTTCCACGCCCGACACGGACCGCTTCGCGGTTGCCTGATCGCATGCGAACGAAGTTGA              | 477 |
| Tw | GTTGGTCTCGGCCAGTTCCACGCCCGACACGGACCGCTTCGCGGTCGCCTGATCGCATGCGACGGTCCCAATACGAAGTTGA    | 480 |
| Ti | CCCGAAAGGCGCTGAGCCGCTGGCAGGACCCTGAGCCCGTGCCGAGTCGTGCCGAGTCGTTTCCTCAAAGTCTCTGCTAGCCGAG | 557 |
| Tw | CCCGAAAGGCGCTGAGCCGCTGGCAGGACACATGAGCCGTGCCGAGTCGTGCCGAGTCGTTTCCTCAAGGTCGTTCCTCAAGGTCGCTAGCCGAG | 560 |
| Ti | CCCGGCTTCCGCCTCCCCCGTAATAGCCCTGTGCCAACCAGAAGTTGCCCAACCAGAATCAGAAGAATGTGAGTCGGCAATAGGCTCGAG | 637 |
| Tw | CCGGGCCTCCGCCTCCCCCCACCCGTAATAGCCCTGTGCCCAACCAGAAGTTGCCCAACCAGAATCAGAATCAGAATGTGGAGTCGGCAATAGGCTCGAG | 640 |
| Ti | CGCCCAATCCGCCACCACCCCCACCGATCCGTGAATCCGGCTCAAAGTGAGCGTGTTCATGGTGTTCATGGTGTTAGCTTGCTGCTTGACC | 717 |
| Tw | CGCCCAATCCGCCACCACCCCCACCGATCCGTGAATCCGTCAAAGTGAGCGTGTTCATGGTGTTCATGGTGTTACTCGTGCTGCTTGACC | 720 |
| Ti | TCTTCAGTGTTGCCCCACCCAGATGCCATTGACGACTCGGCGACATTCGACACTTGATCCGGACACTGTGGTCGGAGAGG     | 797 |
| Tw | TCTTCAGTGTCCGCCACCCCAGATGCCATTGACGACTCGGCGACATTCGACAGTTGACACTGGCCGACACGGTCGGAGAGA    | 800 |
|    | ─────R1─────▶                                                                        |     |
| Ti | AAAGTGTCCGCAATCCGACTTCTTCGCCGATGATGGCCCACTAGCCCGTTCCACCGCAGATGATGAAAGTCAGATTC         | 877 |
| Tw | AAAGTGTCCGCAATCCGACTTCTTCGCCGATGATGGCCCACTAGCCCGTTCCACCGCAGATAATGGAAAGTCGGATTC        | 880 |

*Fig. 1A*

```
Ti  CAGCTTCAAGCTTCCATTCGCGGGGACGGCCAGCCATTACGAAGGCGGTGGCACCTCTCGCCCCAGAACCGATTCGAT    1677
Tw  CAGCTTTAAGCTTCCATTCGCGCGGGACGCCAGCCATTACGAAGGCGGTGGCACCTCTCGCCCCAGAACCGATTCGAT    1680

Ti  TTGGCATTGCAGCGAGCATTTCAGTGATGCTATTTGAACGCCTGGTATTCTCGAAGTCGAGTGGTAGTCCGCCGTGA     1757
Tw  TTGGCATTGCAGCGAGCATTTCAGTAATGCTATTTGAACGCCTGGTATTCTCGAGGTCGAGTGGTAGTCCCGCCGTGA    1760
                                                      Tin-6

Ti  AGCGTGTCAGCCATGCTATGACTATTCGCTGCGGTTCGTCGTTATTGGAGGACCGGCCTTCGGACTGTATGGCATGTCCTT  1837
Tw  AGTGTTGAGCCACGCTATGACCATCGCTGCGGTTCGTCGTTCGTTGTTGAGGACCAGCCTTCGGACTGTATGGCATGTCCTT 1840
        Tin-7

Ti  CATAGCTGAATCGGAAGGGAGATTTGTCCGAGTCCATTCCTGAAGACGGGTGTGACCTGTCGTCGTCCACGATGCT      1917
Tw  TATAGCTGGATCGGAAGGGAGATTTGTCCAGTCCATTGCTGAAGACGGGTGTGACCTGTCGTCGTCCACGATGCT       1920

Ti  CTACATGTCTGGCAGAGACGACTTTCATCGAATAACGAGCTCCCCATACGCCCGACACGAAGACAGTCTCAGCTTCTGT    1997
Tw  CTACATGTCTGGCAGAGACGACTTTCATCGAATAACGAGCTCCCCATACGCCCGACACGAAGACAGTCTCAGCTTCTGT    2000

Ti  ACATAGACTTCGAGCCGATGAATCTCCACTTCGAAAAGAGAGCTTACGACCGGGATCGCCGATGCGTAGAAGGAAAAGACC  2077
Tw  ACATAGACTTCGAGCCGATGAATCTCCACTTCGAAAAGAGAGCTTACGACCGGGATCGCCGATGCGTAGAAGGAAAAGACC  2080

Ti  GACCCTCGTCCCCCTCAAGAGCCAAGAGCCAAGACTGTATGCGGTGGGTATGCGCAGCGTCGCCGACGTATGCAGCCATCCGA  2157
Tw  GACCCCTCGTCCCCCTCAAGAGCCAAGAGCCAAGACTCGTGTGGGTATGCGCAGCGTCGCGAACGTATGCGTAGCATGAGCCATCCGA 2160
                                                                            Tin-8

Ti  CGTAGAGTGGACCGTGCGAAAACGACGAGGCGGACGTTTTTGGAATCAGAGCGGAAAACGGTCGCCTTGGAAGTTGCGGC   2237
Tw  CATAGAGTGGACCGTGCGAAACGACGAGGCGGAGAAGTTTTTGGAATCAGATCAGAGCGGGAGAATGGTCGCCTTGGAAGTTGCGGC 2240

Ti  CGGCTGAGGTGCACTAGCCACTGACCCGCTTCCCAGGCTATGAGACGCAGGTATTACT        (SEQ ID NO:12)   2297
Tw  CGGCTGAGGTGCACTAGCCACTGCCCCGCTGCCCCAGGCTATGAGACGCAGGTATTACT       (SEQ ID NO:13)   2300
                                           Ti-4
```

*Fig. 1C*

METHOD FOR DIFFERENTIATING BETWEEN THE CASUAL AGENTS OF KARNAL BUNT WHEAT FUNGUS AND RYEGRASS SMUT USING PCR

BACKGROUND OF THE INVENTION

1. Field of the Invention

Karnal bunt of wheat is caused by the pathogen *Tilletia indica* Mitra. The ryegrass smut pathogen, closely related to *Tilletia indica*, has been isolated from ryegrass seed and recently identified as *Tilletia walkeri*. This invention relates to novel PCR primers which can be used to detect pathogenic *T. indica* and *T. walkeri* and to particularly distinguish *T. indica* from *T. walkeri*.

2. Description of the Relevant Art

*Tilletia indica* Mitra infects wheat, durum wheat, and triticale and causes a disease commonly referred to as Karnal bunt. The disease was first described in the Indian village of Karnal in 1930 (Mitra, M. 1931. *Ann. Appl. Biol.* 18: 178–179), and since then Karnal bunt has been found in the neighboring countries of Pakistan, Nepal, Iraq, and Afghanistan (Bonde et al. 1996. *Plant Dis.* 80: 1071–1074). In 1972, Karnal bunt was first reported on the North American continent when it was found in Mexico (Duran, R. 1972. *Can. J. Bot.* 50: 2569–2573), and by 1982 the disease had become well established in wheat fields in northwestern Mexico (Bonde et al 1997. *Plant Dis.* 81:1370–1377). Subsequently, in March of 1996, Karnal bunt was discovered in wheat in the United States in Arizona and later that year in California (Bonde et al, 1997, supra; Altschul et al. 1997. *Nuc. Acids Res.* 25: 3389–3402). In 1997, the disease was discovered in a small area of central Texas (Bonde et al., 1997, supra).

Yield reductions in wheat due to Karnal bunt are slight; however, the disease is of extreme economic importance. Many countries, including the United States, have zero tolerance for Karnal bunt and refuse wheat shipments from quarantined countries and/or areas (Palm, M. E. 1999. *Mycologia* 91: 1–12). These measures are based on its seed- and soil-borne nature and the lack of effective chemical control methods. Since the U.S. is the world's leading exporter of wheat with an annual value of $5 billion, Karnal bunt poses a serious threat to international trade for the U.S. wheat industry (Castlebury et al. 1999. *Mycologia* 91: 121–131; Palm, supra). It is therefore desirable to control Karnal bunt at two levels (1) to manage the disease where it occurs so that losses in yield and quality are minimized, and (2) to contain the disease or contaminating teliospores for trade or regulatory purposes (Bonde et al., supra).

Prior to the discovery of Karnal bunt in the U.S., PCR primers were developed to distinguish *T. indica* from other smut fungi, such as *T. barclayana* (sometimes referred to as *T. horrida*) which causes rice kernel smut, that are sometimes present as contaminants in harvested or stored wheat. The technique using PCR primers selected from mitochondrial DNA sequences has been especially useful for differentiating free teliospores of *T. indica* and *T. horrida* that are in the same size range. For example, DNA extracted from mycelia obtained from germinated teliospores washed from wheat seeds can be quickly tested using the primers TI17M1/M2 and TI57M1/M2 (Smith et al. 1996. *Phytopath.* 86: 115–122) and the primers Ti-1/Ti-4 (Ferreira et al. 1996. *Appl. Environ. Microbiol.* 62: 87–93). The primers TI17M1/M2 and TI57M1M2 tested positive with over 78 isolates of *T. indica* and negative with 69 isolates of *T. horrida*. These PCR primers were used to confirm the initial discovery of teliospores in the southwestern U.S. in 1996 as *T. indica*.

During the 1996 National Karnal Bunt Survey conducted by the Animal and Plant Health Inspection Service (APHIS) of the U.S. Department of Agriculture, teliospores that morphologically resembled *T. indica* were discovered as free spores in seed washes of wheat from the southeastern United States and in ryegrass seed lots from Oregon (Bonde et al., 1997, supra; Cunfer et al. 1999. *Plant Dis.* 83: 685–689; Palm, supra). Our existing PCR primers were not able to differentiate between this newly discovered ryegrass smut pathogen and *T. indica*. Recently, the ryegrass smut was described as a new Tilletia species, *T. walkeri*, based upon differences in teliospore morphology and ornamentation (Castlebury et al., supra). Since the morphological differences that distinguish teliospores of *T. indica* from *T. walkeri* require examination of several spores by trained mycologists, this process can be tedious and subject to misinterpretation. Concerns exist that U.S. wheat shipments could be rejected at international ports due to the misidentification of *T. walkeri* teliospores as *T. indica*.

In view of the importance of accurate identification of *T. indica* because of the potential risk of its dissemination in international exchange of germplasm and in international trade, there is a need for improved primers and diagnostic tests which distinguish between *T. indica* and *T. walkeri*, isolated from ryegrass seed, to facilitate implementing specific disease control strategies and for accurately selecting areas for quarantine. Such methods and reagents are valuable tools for monitoring natural disease spread, tracking the soil- and seed-borne fungus in field studies, and detecting the presence of the fungus in grains entering *T. indica*-free areas.

5'-fluorogenic TaqMan PCR assays have been used to detect other pathogenic microorganisms, including plant pathogenic bacteria (Schaad et al. 1999. *Plant Dis.* 83: in press), and viruses (Schoen et al. 1996. *Phytopath.* 86: 993–999), and human fungal pathogens (Brandt et al. 1998. *J. Clin. Microbiol.* 36: 2057–2062; Shin et al 1999. *J. Clin. Microbiol.* 37: 165170); however, this is the first application of the TaqMan system for the detection and identification of plant pathogenic fungi. Since serious economic consequences can result from either erroneously identifying a pathogenic organism or subjecting large agricultural areas to quarantine unnecessarily, the primers, reagents, and assays of the invention will be useful in alleviating discrepancies or resolving disputes that might arise regarding the identity of smut teliospores in wheat shipments.

SUMMARY OF THE INVENTION

We have discovered oligonucleotide sequences which are capable of amplifying DNA fragments specific for identifying the pathogens *Tilletia indica* and *Tilletia walkeri* when used in a simple and rapid PCR assay. These novel primers can be used to differentiate the wheat pathogen *T. indica* from a new Tilletia species, *T. walkeri*, the causative agent of ryegrass smut. The specific diagnosis of *T. indica* is of economic importance because of the need to accurately determine the presence of *T. indica* in grain and grain products to comply with quarantine regulations.

In accordance with this discovery, it is an object of the invention to provide the novel oligonucleotides for use as primers for PCR assays for the specific detection and identification of *T. indica* and *T. walkeri.*

It is a further object of the invention to provide 2.3 kb mitochondrial DNA sequences for *T. indica* and *T. walkeri* and thus a strategy to develop PCR primers based upon the nucleotide differences identified in the 2.3 kb mitochondrial DNA sequences.

It is another object of the invention to provide a TAQ-MAN assay method and a standard PCR assay method utilizing the novel primers.

It is another object of the invention to evaluate and monitor seed treatment protocols utilizing the novel primers.

Other objects and advantages of the invention will become readily apparent from the following description.

DETAILED DESCRIPTION OF THE INVENTION

Figure 1B:
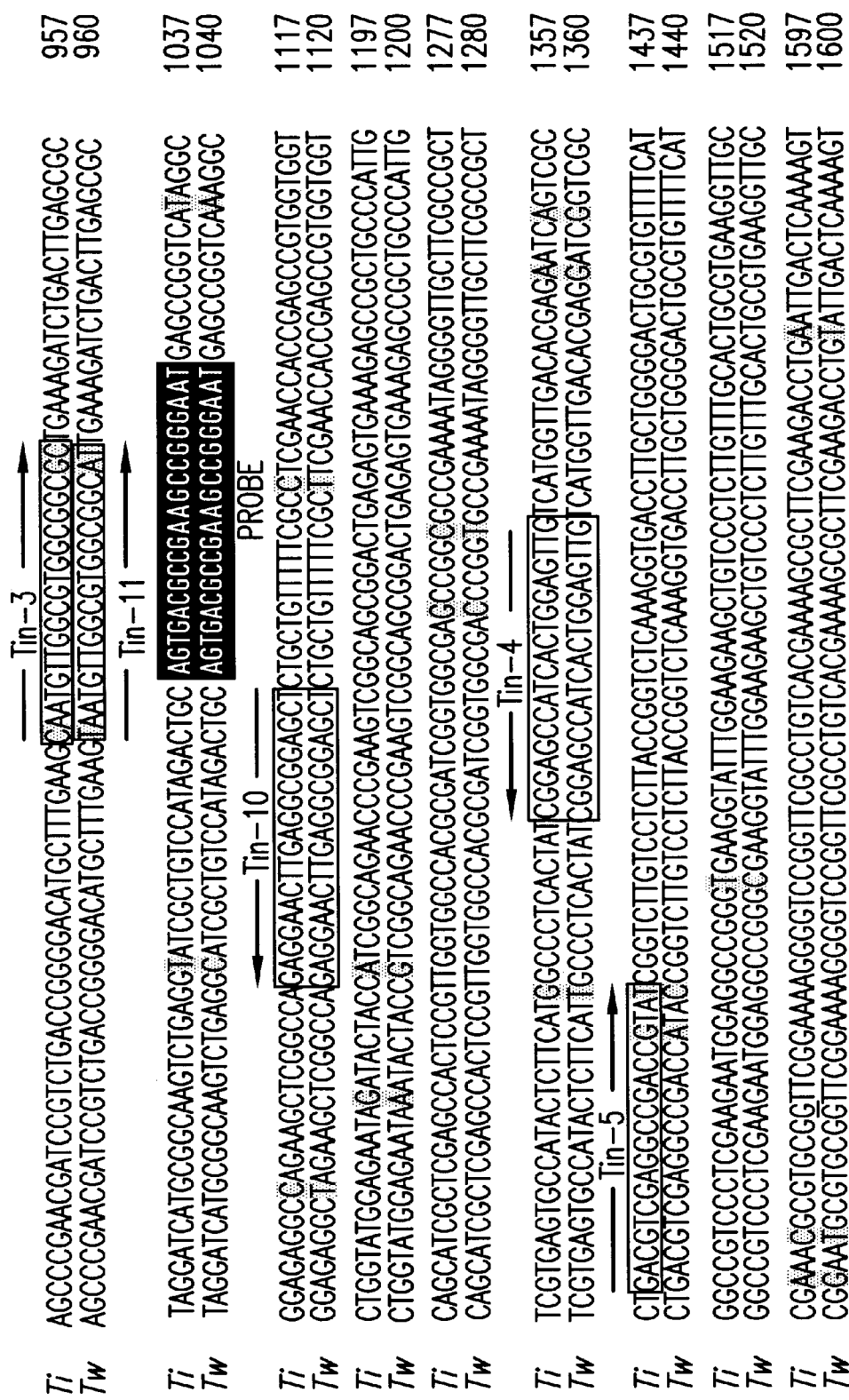
FIG. 1 shows the alignment of the 2.3-kb mitochondrial DNA (mtDNA) sequence from *T. indica* isolate Bpop (Ti) and *T. walkeri* isolate 210G (Tw). Nucleotide differences that occur among either the *T. indica* isolates or the *T. walkeri* isolates are italicized and underlined, while nucleotide differences between *T. indica* and *T. walkeri* isolates are highlighted by shaded boxes. The location of PCR primers is depicted by open boxes, and 5'-to-3' direction of each primer is shown by the arrow. The FAM-labeled TaqMan probe sequence is indicated by the black box. The nucleotide sequences of *T. indica* (Ti) and *T. walkeri* (Tw) are identified by SEQ ID NO:12 and SEQ ID NO:13, respectively. Sequences that are disclosed in the Sequence Listing as having SEQ ID NOs: 2, 4, 5, 7, 10, and 11 are complementary to the reverse orientation of the sequences which are identified as Tin10, R1, Tin6, Tin4, Tin8, and PROBE, respectively, in FIG. 1. SEQ ID NOs: 1, 3, 6, 8, and 9, representing Tin3, F3, Tin5, Tin11, and Tin7, respectively, appear in FIG. 1 as they are disclosed in the Sequence Listing.

Polymerase chain reaction (PCR) has been shown to be a highly sensitive and rapid method for detecting and identifying numerous plant pathogens, including bacteria, viruses, and fungi (Henson et al. 1993. *Ann. Rev. Pytopath.* 31: 81–109). PCR assays are attractive for several reasons. First, the assays are extremely sensitive and highly specific for the pathogen in question. Secondly, PCR tests require minimal amounts of sample material, and several commercial kits are now available for extracting high quality genomic DNA from a wide variety of organisms. Finally, PCR reactions are relatively simple to set up and perform, and results can be obtained within a relatively short period of time, usually within a day. The invention provides for PCR primers, methods, and kits useful for detecting in or on seeds, the pathogen *Tilletia indica*, the causal agent of Karnal bunt on wheat, and further, for differentiating *T. indica* from other Tilletia, particularly *T. walkeri*, the causal agent of ryegrass smut.

Several primers and primer sets have been identified as effective for amplifying particular Tilletia species and to differentiate between species, using standard PCR and preferably the TaqMan detection system. The nucleotide sequence of a 2.3 kb region of mitochondrial DNA (mtDNA) was determined for isolates of *T. indica*, the Karnal bunt pathogen of wheat, and for isolates of the ryegrass smut pathogen. This mtDNA region has been targeted to use to discriminate species of Tilletia. Among the *T. indica* isolates from wheat and the *T. walkeri* isolates obtained from bunted ryegrass seeds, there was greater than 99% identity within this region as determined by the Bestfit program of the Genetics Computer Group computer package (Version 9.0). When comparing the *T. indica* isolates from wheat with the *T. walkeri* isolates, approximately a 3% divergence was observed, i.e., 69 of 2300 base pairs were different. Unique PCR primers were derived from sequences of this region of mtDNA for rapid identification of Tilletia species from wheat and ryegrass. These primers should prove useful for direct detection of the pathogen in a seed health testing program, for several diseases, including Kamal bunt of wheat and ryegrass smut.

A primer can preferably be about twenty and twenty-four nucleotides long. Primers can hybridize to the DNA strand with the coding sequence of a target sequence and are designated sense primers. Primers can hybridize to the DNA strand that is the complement of the coding sequence of a target sequence; such primers are designated anti-sense primers. Primers that hybridize to each strand of DNA in the same location or to one another are known as complements of one another. Primers can be designed to hybridize to a mRNA sequence complementary to a target DNA sequence and are useful in reverse transcriptase PCR.

The primers can hybridize to a target DNA sequence of Tilletia. The target DNA sequence is preferably a mitochondrial DNA region of 2300 bp. The primers can preferably hybridize to particular species of Tilletia and not to other closely related microorganisms. The primers can be used in methods and kits for detecting species of Tilletia in a biological sample, preferably by detecting amplification products using primers that hybridize to the target sequence. The *T. indica*-specific PCR primer sets are: primers Tin3 (5'-CAATGTTGGCGTGGCGGCGC-3'; SEQ ID NO:1)/ Tin10 (5'-AGCTCCGCCTCAAGTTCCTC-3';SEQ ID NO:2); primers F3(5'-GGCACCAGAGTA CAGCTGTCGTT-3'; SEQ ID NO:3)/ R1(5'-GTCGGATTTGCGGACACTTT C-3'; SEQ ID NO:4); primers Tin3 (SEQ ID NO:1)/Tin6 (5'-GGCGGACTACCACTCGAGCT-3'; SEQ ID NO:5); primers Tin5 (5'-GACGTCGAGGCCGACCGTAT-3'; SEQ ID NO:6)/Tin6 (SEQ ID NO:5); and primers Tin3 (SEQ ID NO:1)/Tin4 (5'-CAACTCCAGTGATGGCT CCG-3'; SEQ ID NO: 7). The primer sets comprising Tin11 (5'-TAATGTTGGCGTGG CGGCAT-3'; SEQ ID NO:8/Tin4 (SEQ ID NO:7), Tin7 (5'-GTTTGAGCCACGCTATG ACC-3'; SEQ ID NO:9)/Tin8 (5'-GGCTCATCTACGCATACGTT-3'; SEQ ID NO:10), and Tin 11 (SEQ ID NO:8)/ Tin10 (SEQ ID NO:2) specifically recognize ryegrass smut, *T. walkeri*. The primers of the invention can be used for evaluating and monitoring the efficacy of any treatments utilized to eliminate the pathogenic *T. indica*. The primers of the invention can be used to form probes.

In brief, the DNA amplification products can be detected by (a) providing a biological sample comprising extracted DNA; (b) amplifying a target sequence of the DNA to provide DNA amplification products carrying a selected target DNA sequence; and (c) detecting the presence of *T. indica* and *T. walkeri* species by detecting the presence of the DNA amplification products.

The biological sample may be extracted genomic DNA. The biological sample may be a test sample containing extracted DNA. The biological sample may be ungerminated teliospores. Direct PCR amplification using ungerminated Tilletia teliospores has been reported (McDonald et al. 1999. *Can. J. Plant Pathol.* 21: 78–80); however, PCR amplification from teliospores has been found to be inconsistent. Therefore, currently, extracted DNA is utilized to detect DNA amplification products.

In the preferred method, the enzymatic amplification of the DNA sequence is by polymerase chain reaction (PCR), as described in U.S. Pat. No. 4,683,202 to Mullis, herein incorporated by reference. In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence. Amplified products are optionally separated by methods such as agarose gel electrophoresis. The amplified products can be detected by either staining with ethidium bromide silver stain or by hybridization to a probe. In an alternative embodiment, at least one probe that hybridizes to the amplified products is labeled with a biotin moiety and/or at least one probe labeled with fluorescently-labeled probe. The hybrids are then bound to a solid support such as a bead, multiwell plate, dipstick or the like that is coated with streptavidin. The presence of bound hybrids can be detected using an antibody to the fluorescent tag conjugated to horseradish peroxidase. The enzymatic activity of horseradish peroxidase can be detected with a colored, luminescent or fluorimetric substrate. Conversion of the substrate to product can be used to detect and/or measure the presence of *T. indica* PCR products.

Other methods of PCR using various combination of primers including a single primer to about three primers are known to those of skill in the art and are described in Maniatis (1989. *Molecular Cloning: A Laboratory Manual*. Cold Spring Harbor, N.Y.). Those methods include asymmetric PCR, PCR using mismatched or degenerate primers, reverse transcriptase PCR, arbitrarily primed PCR (Welsh et al. 1990. *Nucleic Acids* Res. 18: 7213–7218), or RAPD PCR, IMS-PCR (Islam et al. 1992. *J. Clin. Micro.* 30: 2801–2806), multiwell PCR (ELOSA) (Luneberg et al. 1993. *J. Clin. Micro.* 31: 1088–1094), and Katz et al. 1993. *Am. J. Vet. Res.* 54:2021–2026). The methods also include amplification using a single primer as described by Judd et al. 1993. *Appl. Env. Microbiol* 59:1702–1708).

An oligonucleotide primer preferably has a gene sequence that hybridizes to a sequence flanking one end of the DNA sequence to be amplified. The DNA sequence to be amplified is located adjacent the attachment of the single primer, or between the attachment of the two primers. In the use of a pair of oligonucleotide primers, each of the primers has a different DNA sequence and hybridizes to sequences that flank either end of the target sequence to be amplified. Design of primers and their characteristics have been described previously. The preferred DNA sequence of the oligonucleotide primer is positive-sense 5'-GGCACCAGAGTACAGCTGTCGTT' (F3;SEQ ID NO:3), negative sense 5'-GTCGGATTTGCGGACACTTTC-3' (R1;SEQ ID NO:4), positive sense 5'-CTAAGTTGGCGTGGCGGCGC-3' (Tin3;SEQ ID NO:1), positive sense 5'-GACGTCGAGGCCGACCGTAT (Tin5;SEQ ID NO:6), negative sense 5'-GGCGGACTA CCACTCGAGCT-3' (Tin6;SEQ ID NO:5), positive sense 5'-GTTTGAGCCACGCTATG ACC-3' (Tin7;SEQ ID NO:9), negative sense 5'-GGCTCATCTACGCATACGTT-3'(Tin8;SEQ ID NO:10), positive sense 5'-TAATGTTGGCGTGGCGGCAT-3' (Tin11;SEQ ID NO:8), negative sense 5'-CAACTCCAGTGATGGCTCCG-3'(Tin4;SEQ ID NO:7), and negative sense 5'-AGCTCCGCCTCAAGTTCCTC-3'(Tin10;SEQ ID NO:2) or complements thereof, or mixtures thereof. The primers may also be degenerate primers that hybridize to the target DNA sequence under hybridization conditions for a primer of that size and sequence complementarity.

The amplified DNA product is optionally separated from the reaction mixture and then analyzed. The amplified gene sequence may be visualized, for example, by electrophoresis in an agarose or polyacrylamide gel or by other like techniques, known and used in the art.

The amplified gene sequence may be directly or indirectly labeled by incorporation of an appropriate visualizing label, as for example, a radioactive, colorimetric, fluorometric or luminescent signal, or the like. In addition, the gel may be stained during or after electrophoresis with a visualizing dye such as ethidium bromide or silver stain wherein the resulting bands by be visualized under ultraviolet light.

To conclusively prove the identity of the amplified DNA product, a Southern blot assay should be conducted. The amplified products are separated by electrophoresis on a polyacrylamide or agarose gel, transferred to a membrane such as a nitrocellulose or nylon membrane, reacted with an oligonucleotide probe, and stained as above. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labeled amplified product is added, reacted, washed to remove unbound substance, and a labeled amplified product attached to the probe or the gene sequence imaged by standard methods.

In addition to developing classical PCR assays, a set of the *T. indica* -specific and *T. walkeri*-specific PCR primers were used with an internal 5'-FAM-labeled oligonucleotide probe sequence in a 5'-fluorogenic TaqMan PCR assay. In most 5'-fluorogenic TaqMan PCR assays, the flanking PCR primers are the same, and the internal fluorescent-labeled probe is designed to be characteristic for a specific sequence (Livak et al. 1995. *PCR Meth. Applic.* 4: 357–362). Since the nucleotide differences within the 2.3-kb mtDNA region of *T. indica* and *T. walkeri* are randomly scattered, the same probe sequence was used for both *T. indica* and *T. walkeri*, however, different flanking primers were used to provide the specificity to distinguish *T. indica* and *T. walkeri* isolates. For TaqMan PCR, the DNA sequences of the oligonucleotide primer sets are positive-sense (forward) 5'-CAATGTTGGCGTGGCGGCGC-3' (Tin3;SEQ ID NO:1) and negative sense (reverse) 5'-AGCTCCGCCTCAAGTTCCTC-3' (Tin10; SEQ ID NO:2) for *T. indica*, and positive sense (forward) 5'-TAATGTTGGCGTGGCGGCAT-3' (Tin11; SEQ ID NO:8) and negative sense (reverse) 5'-AGCTCCGCCTCAAGTTCCTC-3' (Tin10; SEQ ID NO:2) (*T. walkeri*-specific) and or complements thereof, or mixtures thereof. An internal oligonucleotide, a 25-mer probe, was labeled with the chromophore FAM: 5'-FAM-ATTCCCGGCTTCGGCGTCACT-TAMRA-3' (SEQ ID NO:11). Primer Tin3 provides specificity for *T. indica* isolates, while Tin11 is used for *T. walkeri* isolates. In both PCR assays, Tin10 is used with either Tin3 or Tin11, and the size of both amplicons is 212 bp.

The TaqMan detection assays offer several advantages over the classical PCR assays developed for *T. indica* or *T. walkeri*. First, the TaqMan assays combine the sensitivity of PCR along with hybridization of the internal oligonucleotide sequence that is present in a *T. indica* or *T. walkeri* mtDNA sequence. Following PCR, samples do not have to be separated on agarose gels, and the subsequent Southern blots and hybridization steps that are necessary to verify the identity of the PCR products is eliminated. These additional post-PCR confirmation steps can easily add several days for an accurate identification. Using the TaqMan system, the *T. indica*- or *T. walkeri*-specific 5'-fluorogenic assays are completed within 2.5 h. Further, the methodology involved in the assay process makes possible the handling of large numbers of samples efficiently and without cross-contamination and is therefore adaptable for robotic sampling. As a result, large numbers of test samples can be processed in a very short period of time using the TaqMan assay. Time can be a very important factor when wheat shipments are being held at port due to the presence of smut teliospores. Another advantage of the TaqMan system is the potential for multiplexing. Since different fluorescent reporter dyes can be used to construct probes, several different pathogen systems could be combined in the same PCR reaction, thereby reducing the labor costs that would be incurred if each of the tests were performed individually. The advantages of rapid, conclusive data together with labor and cost efficiency make the TaqMan detection system utilizing the specific primers of the invention a highly beneficial system for monitoring seed pathogens, especially in those circumstances where seed screening results have major commercial and trade consequences.

The primers and amplification method can further be useful for evaluating and monitoring the efficacy of any treatments utilized to eliminate the pathogenic *T. indica*. In this method, biological samples are obtained from seeds prior to treatment and from seeds which have undergone treatment with a treatment protocol designed to eradicate *T. indica*. In addition, biological samples can be obtained from seeds at several time points during treatment. DNA amplification products of a target sequence of *T. indica* from all samples are analyzed for the presence of *T. indica*. Results from samples obtained prior, during and after treatment are compared in order to determine efficacy of the treatment protocol.

Similarly, the novel primers and methods are very useful for epidemiology and host-pathogen studies.

EXAMPLES

Example 1

Fungal Isolates and Growth Conditions

A list of the Tilletia isolates used in this study is shown in Table 1. The isolates are from either bunted seed samples or seed washes, and the origin is noted. Mycelial cultures were grown on potato dextrose agar (PDA) plates at 21° C. for 7 to 10 days. Secondary sporidia were produced by placing mycelial plugs onto 2% water-agar plates and incubating at 21° C. for 3 to 4 days. Mycelial tissue used for extracting genomic DNA was grown by placing mycelial plugs cut from water-agar plates onto the lid of a petri plate containing potato dextrose broth and incubating at 21° C. for 10 to 15 days. Mycelial mats were harvested by filtration through a Buchner funnel onto Whatman filter paper, and the tissue was blotted dry and stored at −80° C.

TABLE 1

Tilletia isolates

| Isolate | Sample Composition | Origin | Year |
|---|---|---|---|
| *T. walkeri* | | | |
| 210G | seed wash | Oregon | 1997 |
| BPPC-0410 | composite | Oregon | 1997 |
| BPPC-0518 | teliospore | Georgia | 1997 |
| BPPC-0519 | teliospore | Georgia | 1997 |
| YRG-001 | teliospore | Oregon | 1997 |
| YRG-002 | teliospore | Oregon | 1997 |
| YRG-009 | teliospore | Oregon | 1997 |
| TNRG-02 | teliospore | Tennessee | 1997 |
| TNRG-03 | teliospore | Tennessee | 1997 |
| TNRG-10 | teliospore | Tennessee | 1997 |
| *T. indica* | | | |
| Bpop | composite | Pakistan | 1985 |
| B4 | teliospore | Pakistan | 1985 |
| B4-S3 | basidiospore | Pakistan | 1985 |
| B4-S5 | basidiospore | Pakistan | 1985 |
| A3 | teliospore | India | 1991 |
| A1-S3 | basidiospore | India | 1991 |
| A1-S4 | basidiospore | India | 1991 |
| A1-S5 | basidiospore | India | 1991 |
| A4-S4 | basidiospore | India | 1991 |
| Pantanagar 1991 | composite | India | 1991 |
| Sangar | composite | India | 1983 |
| WL1562 | composite | India | 1983 |
| Sample IIb | teliospore | India | 1989 |
| HD2288 | teliospore | India | 1989 |
| WL711 | teliospore | India | 1989 |
| WL2265 | teliospore | India | 1989 |
| Mx-81A | teliospore | Mexico | 1981 |

TABLE 1-continued

Tilletia isolates

| Isolate | Sample Composition | Origin | Year |
|---|---|---|---|
| D3 1981 Sonora | teliospore | Mexico | 1981 |
| D3-S1 | basidiospore | Mexico | 1981 |
| D3-S2 | basidiospore | Mexico | 1981 |
| D3-S3 | basidiospore | Mexico | 1981 |
| D3-S4 | basidiospore | Mexico | 1981 |
| Mx-82 | composite | Mexico | 1982 |
| Mx-85 | composite | Mexico | 1985 |
| Ciano 1982 | teliospore | Mexico | 1982 |
| Calexico | teliospore | Mexico | 1983 |
| Mexicali CF | composite | Mexico, CA | 1990 |
| Navajoa 1989 Mx | composite | Mexico | 1989 |
| Yv3b | teliospore | Mexico | 1989 |
| Yv3c | teliospore | Mexico | 1989 |
| Mv-1a | teliospore | Mexico | 1989 |
| Mv-1c | teliospore | Mexico | 1989 |
| Fv-1c | teliospore | Mexico | 1989 |
| Brazil T5 | teliospore | Brazil | 1991 |
| *T. barclayana* | | | |
| PJ-11 | basidiospore | China | 1996 |
| L201 | basidiospore | California | 1985 |
| AK-T2 | composite | Arkansas | 1986 |
| P-5 | basidiospore | Philippines | 1989 |
| 137al | basidiospore | Brazil | 1992 |
| Tsp14 | basidiospore | California | 1982 |
| Tsp5 | basidiospore | Washington | 1982 |
| *T. caries* | | | |
| C-100 | composite | Washington | 1990 |
| C-125 | composite | Idaho | 1990 |
| *T. laevis* | | | |
| F-008 | composite | Oklahoma | 1989 |
| *T. controversa* | | | |
| DB-107 | composite | Idaho | 1989 |
| DB-035 | composite | Canada | 1989 |
| DB-046 | composite | Czechoslovakia | 1989 |
| DB-131 | composite | Montana | 1989 |
| *T. fusca* | | | |
| G-110 | composite | Idaho | 1990 |
| G-112 | composite | Oregon | 1990 |
| G-105 | composite | Utah | 1990 |

Example 2

DNA Extraction and Recombinant DNA Techniques

Genomic DNA from *T. indica* and *T. walkeri* was extracted from 0.5 to 1.0 g frozen mycelial tissue. The tissue was placed into 1.5 ml micro-centrifuge tubes with 75 μl lysis buffer, ground by means of a sterile pestle attached to a power drill, a second 75 μl lysis buffer added, and DNA extracted using a Puregene Genomic DNA Isolation kit (Gentra Systems) according to the manufacturer's directions. DNA concentrations were determined by UV spectrophotometry at 260 nm.

A 2.3-kb fragment was amplified from three *T. indica* isolates (Yv3b, WL 1562, and Bpop) and *T. walkeri* isolates (210G, YRG-001, and TNRG-02) by PCR using the oligonucleotide primers Ti-1 and Ti-4 (Life Technologies/Gibco BRL, Gaithersburg, Md.) as described previously. The fragments from these isolates were cloned into the TA cloning vector pCR2.1 (Invitrogen Corp., Carlsbad, Calif.) and transformed into *E. coli* INVαF' cells according to the manufacturer's directions.

Example 3

DNA Sequencing and Analysis

Plasmid DNA containing the 2.3-kb mtDNA fragment from *T. indica* or *T. walkeri* isolates was extracted from *E. coli* using a Qiagen Plasmid DNA kit following the manufacturer's procedure (Qiagen, Inc., Chatsworth, Calif.). DNA concentrations were determined by UV spectrophotometry at 260 nm, and nucleotide sequence was determined (Sequetech Corp., Mountain View, Calif.). Nucleotide sequences were compared and aligned in our laboratory using the Bestfit and Pileup programs of the Genetics Computer Group computer package (Version 9.0)(Deverex et al. 1984. *Nucleic Acids Res.* 12: 387–395) at the Advanced Biomedical Computing Center of the National Cancer Institute, Frederick, Md. Comparisons were made among the isolates from the same species and between the two Tilletia species.

Among the three *T. indica* isolates, only two differences were found among the 2297 nucleotides (>99.9% similarity). Likewise, when the three *T. walkeri* sequences were analyzed, 13 differences were observed among the 2300 nucleotides (99.4% similarity). However, a comparison between the *T. indica* and *T. walkeri* sequences revealed 69 nucleotide differences (FIG. 1). Most of the nucleotide differences between *T. indica* and *T. walkeri* were randomly scattered throughout the 2.3-kb region, however, three nucleotides (CAG) were found to be missing in all *T. indica* sequences corresponding to nucleotide positions 214–217 in *T. walkeri*. Blast searches of nucleic acid and protein databases with the *T. indica* and *T. walkeri* 2.3-kb mtDNA sequences did not reveal any significant matches with any sequences in either database (Altschul et al., supra).

Example 4

Selection of Species-Specific Primers and the Development of Polymerase Chain Reaction Assays Although the overall sequence similarity is high between *T. indica* and *T. walkeri* within this mtDNA region (97.0% similarity), selective PCR primer sites were chosen to distinguish these two Tilletia species from each other using PCR. Oligonucleotide primers specific to either *T. indica* or *T. walkeri* were synthesized (Life Technologies/Gibco BRL, Gaithersburg, Md.). Primers were designed to incorporate differences at the final nucleotide position at the 3'-end of the oligonucleotide. Because Taq polymerase does not extend primers with 3'-terminal mismatches (Mullis et al. 1989. *Methods in Enzymology* 155: 335–350), PCR products are produced only in those reactions where complete annealing occurs at the 3'-end between the DNA template and the oligonucleotide primer. Using this strategy, five sets of PCR primers were designed to regions where there is a conserved nucleotide among the three *T. indica* isolates but not among the three *T. walkeri* isolates. The five primer sets designed specifically for *T. indica* are: Tin 3 (5'-CAATGTTGGCGTGGCGGCGC-3'; SEQ ID NO:1)/Tin 10 (5'-AGCTCCGCCTCMGTTCCTC-3'; SEQ ID NO:2), F3 (5'-GGCACC AGAGTACAGCTGTCGTT-3'; SEQ ID NO:3)/R1(5'-GTCGGATTTGCGGACACTTTC-3'; SEQ ID NO:4), Tin3/Tin6 (5'-GGCGGACTACCACTCGAGCT-3';SEQ ID NO:5), Tin5 (5'-GACGTCGAGGCCGACCGTAT-3'; SEQ ID NO:6)/Tin6, and Tin3/Tin4 (5'-CAACTCCAGTGATGGCTCCG -3'; SEQ ID NO:7). Similarly, three sets of PCR primers were selected as *T. walkeri*-specific, based upon characteristic nucleotides at the final nucleotide position at the 3'-end of the oligonucleotide. The *T. walkeri*-specific PCR primer sets are: Tin 11 (5'-TAATGTTGGCGTGGCGGCAT-3'; SEQ ID NO:8)/Tin4, Tin11/Tin10 (5'-AGCTCCGCCTCAAGTTCCTC-3'; SEQ ID NO:2), and Tin7 (5'-GTTTGAGCCACGCTATGACC-3'; SEQ ID NO:9)/Tin8 (5'-GGCTCATCTACGCATAC GTT-3'; SEQ ID NO:10). Sequences that are disclosed in the Sequence Listing as having SEQ ID NOs: 2, 4, 5, 7, 10, and 11 are complementary to the reverse orientation of the sequences which are identified as Tin10, R1, Tin6, Tin4, Tin8, and PROBE, respectively, in FIG. 1. SEQ ID NOs: 1, 3, 6, 8, and 9, representing Tin3, F3, Tin5, Tin11, and Tin7, respectively, appear in FIG. 1 as they are disclosed in the Sequence Listing.

Example 5

Polymerase Chain Reaction and Southern Blot Analysis

Classical PCR reactions were performed in a Gene AMP PCR System 9700 thermocycler (Perkin-Elmer/Applied Biosystems, Inc., Foster City, Calif.) using 25 ng of genomic DNA. PCR was performed in a total volume of 25 µl containing: 10 nM Tris-HCl; 50 mM KCL (pH 8.3); 1.5 mM $MgCl_2$; 0.001% (w/v)gelatin; dATP, dGTP, dCTP, and dTTP each at a concentration of 100 µM; each primer at a concentration of 100 nM; and 0.5 U of Amplitaq DNA polymerase (Perkin-Elmer/Applied Biosystems). PCR reaction conditions were optimized for each set of PCR primers by adjusting the annealing temperature or the number of amplification cycles. The *T. indica*-specific PCR primers Tin3/Tin 10, F3/R1, Tin3/Tin6, Tin5/Tin6, and Tin3/Tin4 were used with the following cycling conditions: 94° C. denaturation for 1 min, 25 cycles of 94° C. for 15 sec, 65° C. for 15 sec, and 72° C. for 15 sec, followed by an extension step of 72° C. for 6 min. The *T. walkeri*-specific PCR primers Tin11Tin4 were used at the same conditions as described for the *T. indica*-specific PCR primers; however, for the *T. walkeri* primers Tin7/Tin8, the number of cycles was increased to 30. For the *T. walkeri* primer Tin11/Tin10, an annealing temperature of 55° C. was employed for 45 cycles. Negative controls (no template DNA) were tested by using the same reaction mixture under the amplification conditions described above without template DNA. To verify that DNA extracted from *T. indica* and *T. walkeri* isolates could be amplified by PCR, primers ITS2 and ITS5 (White et al. 1990. In: PCR Protocols (Innis et al., Eds.), Academic Press, Inc., San Diego, Calif., pages 315–322) were used to amplify an internal transcribed spacer region of the rDNA. DNA fragments produced by PCR were analyzed by electrophoresis on 1.4% agarose gels in 0.5×TBE buffer stained with ethidium bromide (Ausubel et al., Eds. 1987. Current Protocols in Molecular Biology, John Wiley, New York, N.Y.).

Gels for Southern blots were denatured and blotted onto positively charged nylon membranes (Boehringer-Mannheim, Indianapolis, Ind.) by capillary transfer using 10×SSC, and DNA was bound to nylon membranes by UV-cross linking (Ausubel et al., supra). The membranes were prehybridized at 55° C. for 2 h in roller bottles containing Dig Easy Hybridization Solution (Boehringer-Mannheim) in a hybridization oven (Hybaid, Inc., Franklin, Mass.). A probe of the 2.3-kb mtDNA region from *T. indica* isolate WL1562 was labeled with digoxigenin using PCR according to the manufacturer's directions (Boehringer-Mannheim). Fifty ng of denatured digoxigenin-labeled probe DNA was added to each roller bottle, and the hybridizations were performed for 14–16 h at 55° C. The filters were washed twice in 2×SSC, 0.1% SDS at room temperature for 5 min followed by two washes in 0.2×SSC, 0.1% SDS at 68° C. for 15 min. Chemiluminescent detection was performed as directed by the manufacturer (Boehringer-Mannheim), and the membranes were exposed to X-ray film (Blue sensitive; Molecular Technologies, St. Louis, Mo.) at room temperature for up to 20 min.

Figure 2:
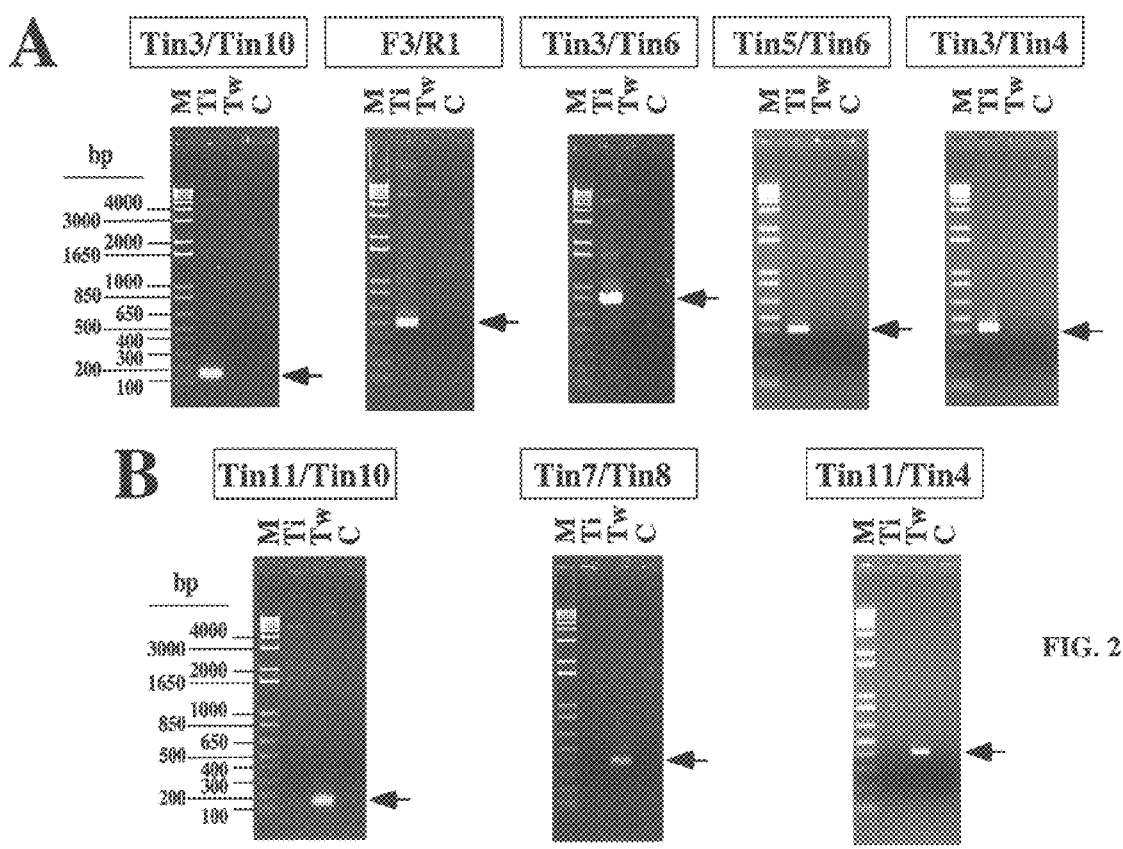
FIG. 2 shows agarose gels of classical PCR assays using *T. indica* -specific (A) or *T. walkeri*-specific (B) primers. M indicates molecular weight markers; Ti, *T. indica* isolate Bpop; Tw, *T. walkeri* isolate YRG-001; and C, no DNA template control. PCR products are indicated by arrows.

In order to verify the specificity of the *T. indica* and *T. walkeri* primers, DNA extracted from *T. indica* and *T. walkeri* isolates from different geographic areas was tested with each PCR primer set. The five *T. indica* PCR primer sets produced single bands using DNA from all 34 *T. indica* isolates. The *T. indica*-specific primers Tin3Tin6, Tin3/Tin10, Tin3/Tin4, Tin5/Tin6, and F3/R1, amplified DNA fragments of: 885, 212, 414, 392, and 497 bp, respectively (FIG. 2A). None of the 10 isolates of *T. walkeri* produced a PCR product (Table 1). Southern blot hybridizations confirmed the identity of the PCR product for each of the *T. indica* samples, and no detectable bands were observed with any of the *T. walkeri* samples (Southern blots not shown). Similarly, the three *T. walkeri* PCR primers produced single bands only with DNA extracted from *T. walkeri* samples. The *T. walkeri* primers Tin11/Tin10, Tin11/Tin4, and Tin7/Tin8 amplified PCR products of 212, 414, and 391, respectively (FIG. 2B). No detectable product was found with DNA from the *T. indica* isolates (Southern blots not shown).

TABLE 2

Species and strains and results of PCR with primer sets SEQ ID NOS: 1 & 2, 1 & 5, 6 & 5, 1 & 7, and 3 & 4 of *T. indica* and with the primer sets SEQ ID NOS: 9 & 10, 8 & 7, and 8 & 2 of *T. walkeri*.

| Isolate[a] | PCR-Amplification Primer Sets (SEQ ID NOs) | | | | | | | |
|---|---|---|---|---|---|---|---|---|
| | 1 & 2[b] | 1 & 5[c] | 6 & 5[d] | 1 & 7[e] | 3 & 4[f] | 9 & 10[g] | 8 & 7[h] | 8 & 2[i] |
| *T. indica* | | | | | | | | |
| Bpop | + | + | + | + | + | − | − | − |
| B4 | + | + | + | + | + | − | − | − |
| B4-S3 | + | + | + | + | + | − | − | − |
| B4-S5 | + | + | + | + | + | − | − | − |
| A3 | + | + | + | + | + | − | − | − |
| A1-S3 | + | + | + | + | + | − | − | − |

TABLE 2-continued

Species and strains and results of PCR with primer sets SEQ ID NOS: 1 & 2, 1 & 5, 6 & 5, 1 & 7, and 3 & 4 of *T. indica* and with the primer sets SEQ ID NOS: 9 & 10, 8 & 7, and 8 & 2 of *T. walkeri*.

| Isolate[a] | 1 & 2[b] | 1 & 5[c] | 6 & 5[d] | 1 & 7[e] | 3 & 4[f] | 9 & 10[g] | 8 & 7[h] | 8 & 2[i] |
|---|---|---|---|---|---|---|---|---|
| A1-S4 | + | + | + | + | + | − | − | − |
| A1-S5 | + | + | + | + | + | − | − | − |
| A4-S4 | + | + | + | + | + | − | − | − |
| Pantanagar 1991 | + | + | + | + | + | − | − | − |
| Sangar | + | + | + | + | + | − | − | − |
| WL 1562 | + | + | + | + | + | − | − | − |
| Sample IIb | + | + | + | + | + | − | − | − |
| HD2288 | + | + | + | + | + | − | − | − |
| WL711 | + | + | + | + | + | − | − | − |
| WL2265 | + | + | + | + | + | − | − | − |
| Mx-81 | + | + | + | + | + | − | − | − |
| Mx-81A | + | + | + | + | + | − | − | − |
| D3 1991 Sonora | + | + | + | + | + | − | − | − |
| D3-S1 | + | + | + | + | + | − | − | − |
| D3-S2 | + | + | + | + | + | − | − | − |
| D3-S3 | + | + | + | + | + | − | − | − |
| D3-S4 | + | + | + | + | + | − | − | − |
| Mx-82 | + | + | + | + | + | − | − | − |
| Mx-85 | + | + | + | + | + | − | − | − |
| Ciano 1982 | + | + | + | + | + | − | − | − |
| Calexico | + | + | + | + | + | − | − | − |
| MexicaliCF | + | + | + | + | + | − | − | − |
| Navajoa 1989 Mx | + | + | + | + | + | − | − | − |
| Yv3b | + | + | + | + | + | − | − | − |
| Yv3c | + | + | + | + | + | − | − | − |
| Mv-1a | + | + | + | + | + | − | − | − |
| Mv-1c | + | + | + | + | + | − | − | − |
| Fv-1c | + | + | + | + | + | − | − | − |
| Brazil T5 | + | + | + | + | + | − | − | − |
| *T. walkeri* | | | | | | | | |
| 210G | − | − | − | − | − | + | + | + |
| BPPC-0410 | − | − | − | − | − | + | + | + |
| BPPC-0518 | − | − | − | − | − | + | + | + |
| BPPC-0519 | − | − | − | − | − | + | + | + |
| YRG-001 | − | − | − | − | − | + | + | + |
| YRG-002 | − | − | − | − | − | + | + | + |
| YRG-003 | − | − | − | − | − | + | + | + |
| YRG-004 | − | − | − | − | − | + | + | + |
| YRG-005 | − | − | − | − | − | + | + | + |
| YRG-006 | − | − | − | − | − | + | + | + |
| YRG-007 | − | − | − | − | − | + | + | + |
| YRG-008 | − | − | − | − | − | + | + | + |
| YRG-009 | − | − | − | − | − | + | + | + |
| YRG-010 | − | − | − | − | − | + | + | + |
| YRG-011 | − | − | − | − | − | + | + | + |
| YRG-012 | − | − | − | − | − | + | + | + |
| YRG-013 | − | − | − | − | − | + | + | + |
| YRG-014 | − | − | − | − | − | + | + | + |
| YRG-015 | − | − | − | − | − | + | + | + |
| TNRG-02 | − | − | − | − | − | + | + | + |
| TNRG-03 | − | − | − | − | − | + | + | + |
| TNRG-10 | − | − | − | − | − | + | + | + |
| TNRG-11 | − | − | − | − | − | + | + | + |

[a]Positive results were obtained for all isolates (*T. indica* and *T. walkeri*) when DNA extracts were amplified by the primers ITS2 and ITS5.
[b]Positive result means presence of 212 bp band and negative means no visible band in ethidium bromide stained agarose gel and by Southern blot hybridizations.
[c]Positive result means presence of 885 bp band and negative means no visible band in ethidium bromide stained agarose gel and by Southern blot hybridizations.
[d]Positive result means presence of 392 bp band and negative means no visible band in ethidium bromide stained agarose gel and by Southern blot hybridizations.
[e]Positive result means presence of 414 bp band and negative means no visible band in ethidium bromide stained agarose gel and by Southern blot hybridizations.
[f]Positive result means presence of 497 bp band and negative means no visible band in ethidium bromide stained agarose gel and by Southern blot hybridizations.
[g]Positive result means presence of 391 bp band and negative means no visible band in ethidium bromide stained agarose gel and by Southern blot hybridizations.

TABLE 2-continued

Species and strains and results of PCR with primer sets SEQ ID NOS: 1 & 2, 1 & 5, 6 & 5, 1 & 7, and 3 & 4 of *T. indica* and with the primer sets SEQ ID NOS: 9 & 10, 8 & 7, and 8 & 2 of *T. walkeri*.

| Isolate[a] | PCR-Amplification Primer Sets (SEQ ID NOs) | | | | | | | |
|---|---|---|---|---|---|---|---|---|
| | 1 & 2[b] | 1 & 5[c] | 6 & 5[d] | 1 & 7[e] | 3 & 4[f] | 9 & 10[g] | 8 & 7[h] | 8 & 2[i] |

[h]Positive result means presence of 414 bp band and negative means no visible band in ethidium bromide stained agarose gel and by Southern blot hybridizations.
[i]Positive result means presence of 212 bp band and negative means no visible band in ethidium bromide stained agarose gel and by Southern blot hybridizations.

Example 6

TaqMan 5' Nuclease PCR Assay

Figure 3A:
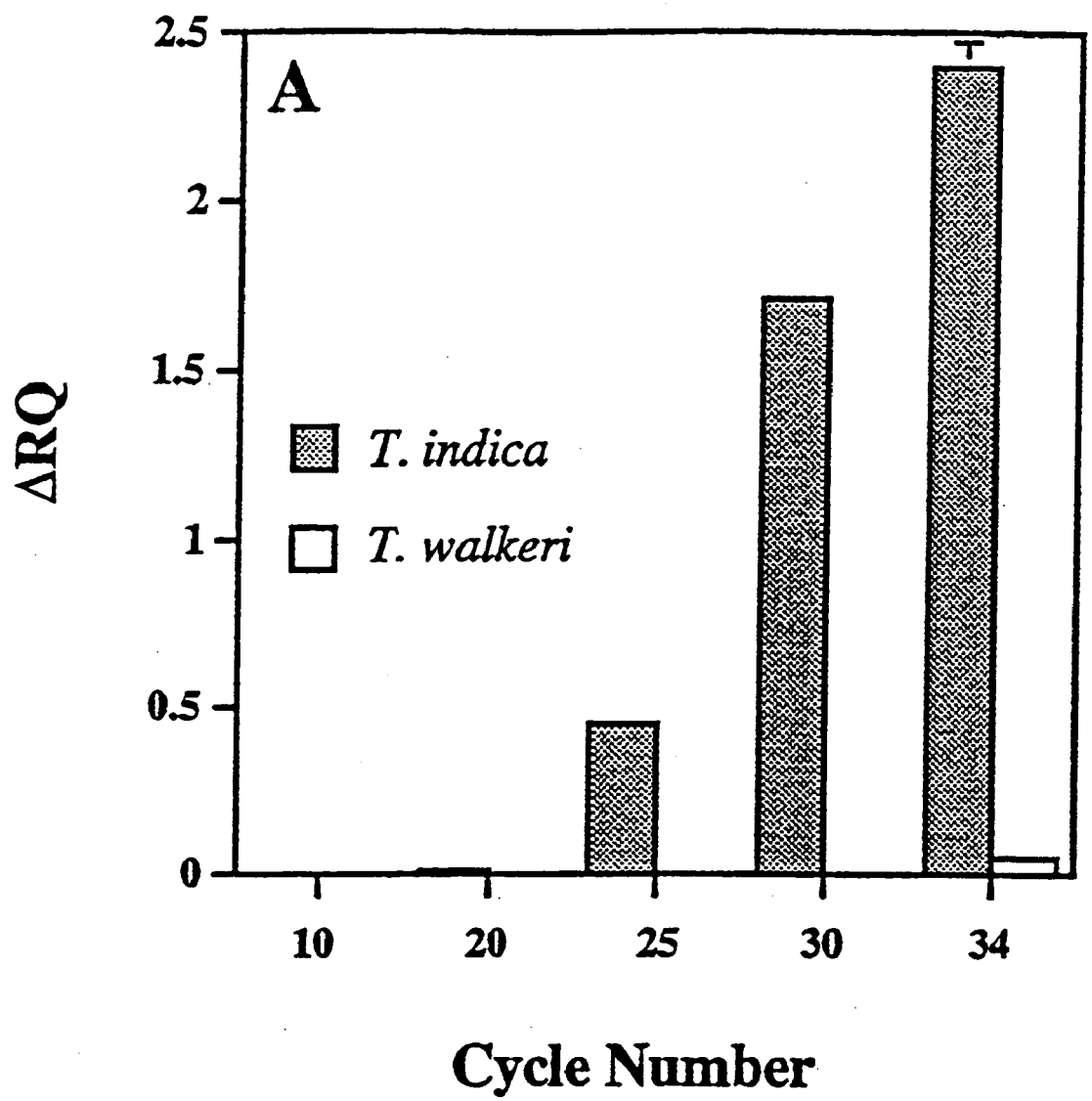
FIG. 3 shows the amplification of mtDNA of *T. indica* isolate Bpop and *T. walkeri* isolate YRG-001 by TaqMan PCR and an ABI Prism 7700 Sequence Detection System. *T. indica*-specific flanking primers Tin3/Tin10 (A) or *T. walkeri*-specific flanking primers Tin11Tin10 (B) were used with a 5'-FAM-labeled internal probe sequence. The left axis (ΔRQ) is the change in fluorescence that is a measure of probe cleavage efficiency, and the bottom axis is the PCR cycling stage. Duplicate DNA samples were analyzed for each isolate. Amplification of mtDNA from *T. indica* is shown in FIG. 3A; baseline values were obtained for *T. walkeri*.
In FIG. 3B, amplification of mtDNA of *T. walkeri* is shown; mtDNA of *T. indica* was not amplified.
Figure 3B:
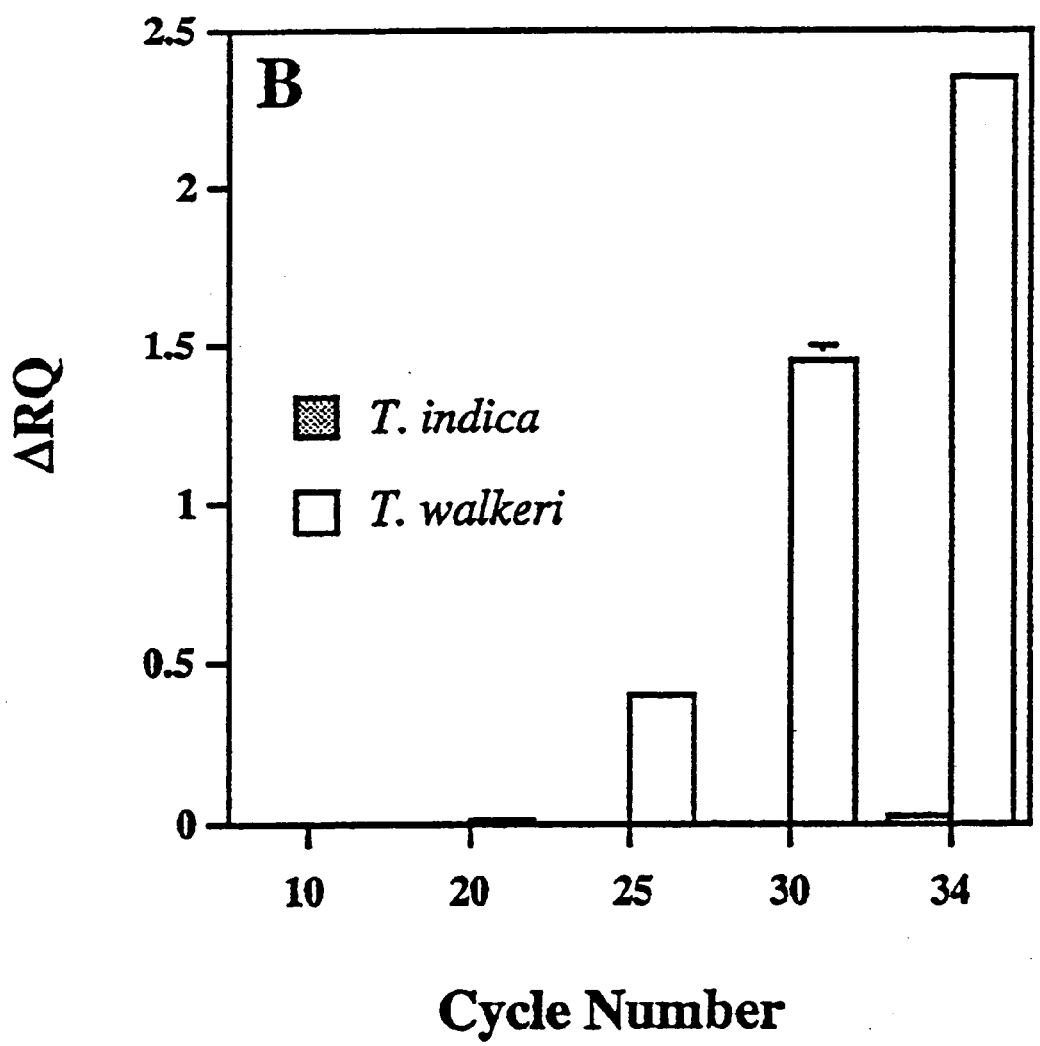

Fluorogenic 5' nuclease assays were developed for the TaqMan system that utilized either the *T. Indica*-specific primer set Tin3/Tin10 or the *T. walkeri* primers Tin11/Tin10 and an internal 5'-FAM-labeled oligonucleotide probe. The PCR conditions were a modification of the classical PCR assays described above for the *T. indica*-specific primers Tin3/Tin11. Cycling conditions consisted of the following: 50° C. for 2 min, 95° C. for 10 min, and 34 cycles of 95° C. for 15 sec, and 60° C. for 1 min. The 5' nuclease assays were performed using an ABI Prism 7700 Sequence Detection system (Perkin-Elmer/applied Biosystems) in a total volume of 25 μl containing 1×TaqMan Universal Master Mix (Perkin-Elmer/Applied Biosystems), 400 nM of either *T. indica*-specific primer set Tin3/Tin10 or the *T. walkeri* primers Tin 11/Tin10, and 12.5 ng of genomic DNA. The TaqMan probe, 5'-FAM-ATTCCCGGCTTCGGCGTCACT-TAMRA-3' (SEQ ID NO:11), was used at 400 nM in both the *T. indica*-specific and the *T. walkeri*-specific assays. In both TaqMan assays, the amplicon was 212 bp. The ΔRQ values were measured at the conclusion of each amplification cycle, and plots of *T. indica* isolate Bpop and *T. walkeri* isolate YRG-001 for the two assays are shown (FIG. 3). In the *T. indica*-specific TaqMan assay, the Bpop samples began to cross the threshold at the $20^{th}$ cycling step, whereas the *T. walkeri* YRG-001 sample did not begin to cross the threshold until the $33^{rd}$ cycling step. Similarly, in the *T. walkeri*-specific TaqMan assay, the YRG-001 sample crossed the threshold at the $20^{th}$ cycle step, while the Bpop sample did not cross the threshold until the $33^{rd}$ cycling step.

Figure 4A:
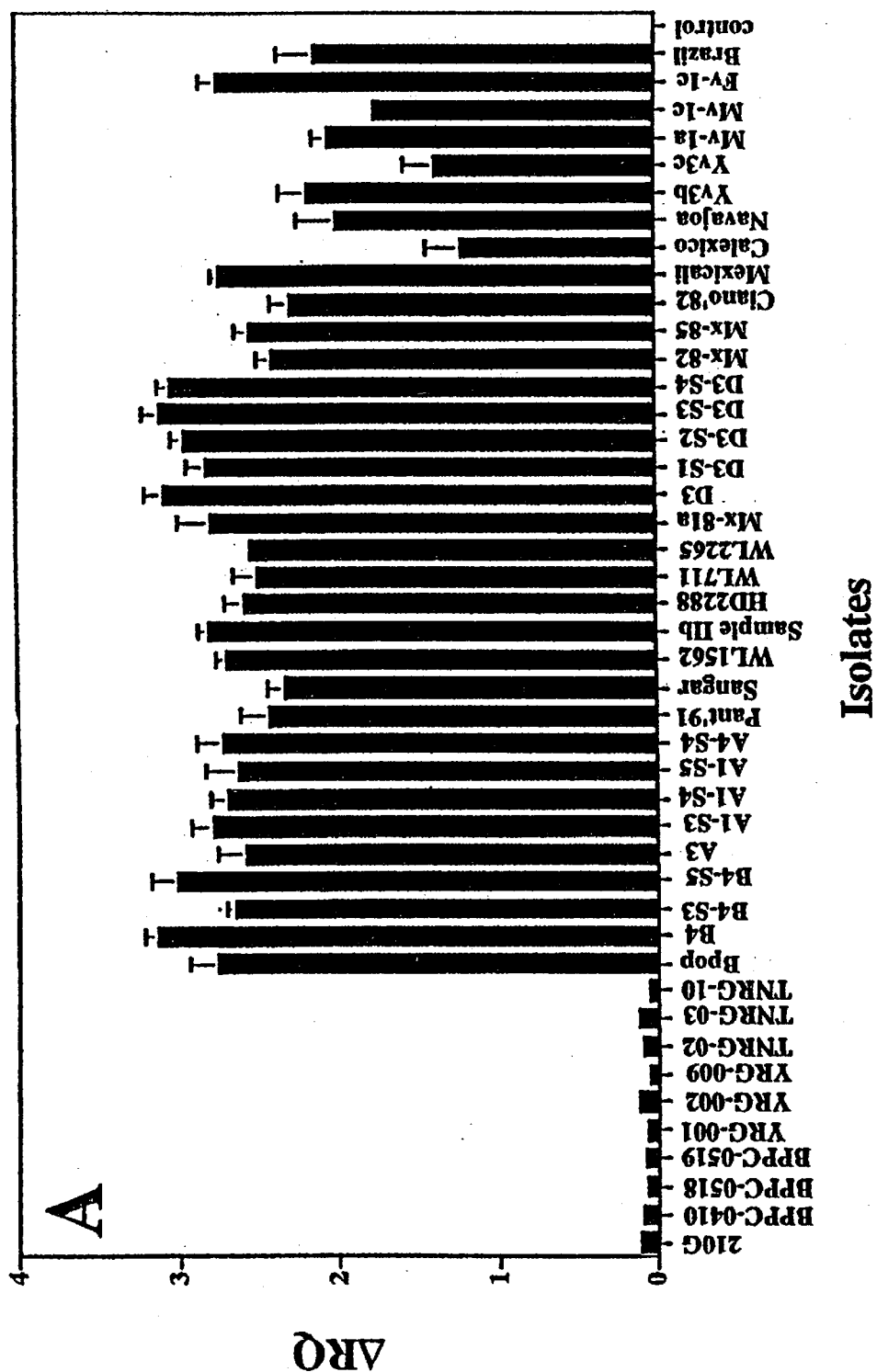
FIG. 4 shows TaqMan PCR amplification of mtDNA of *T. indica* isolates and *T. walkeri* isolates using either the *T. indica*-specific flanking primers Tin3/Tin10 (A) or *T. walkeri*-specific flanking primers Tin11/Tin10 (B) after 34 amplification cycles. The ΔRQ values are the means of two independent experiments with duplicate DNA samples. Error bars represent the standard errors of the means.
Figure 4B:
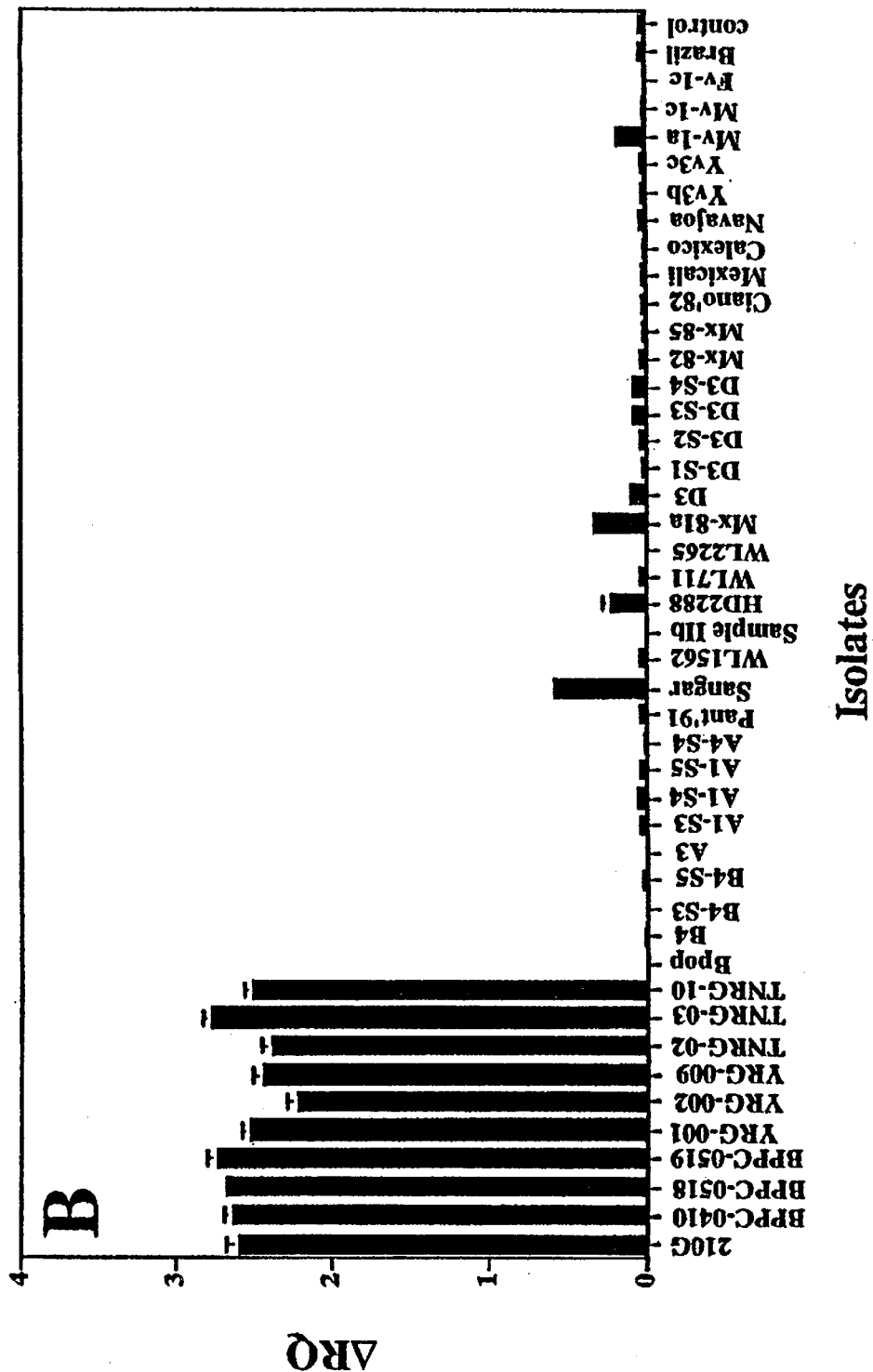

In order to evaluate the accuracy of the two TaqMan assays, DNA extracted from the 34 *T. indica* and 10 *T. walkeri* isolates was tested and compared to the classical PCR assays. For the *T. inidica* TaqMan assay, all 34 *T. indica* isolates displayed ΔRQ values of at least 1.22, whereas none of the 10 *T. walkeri* isolates had ΔRQ values of greater than 0.12 after 34 cycles of amplification (FIG. 4A). Conversely, all 10 *T. walkeri* isolates had ΔRQ values of at least 2.21, while none of the 34 *T. indica* isolates had a ΔRQ value of greater than 0.57 using the *T. walkeri*-specific primers Tin11/Tin10 in the TaqMan assay (FIG. 4B). In both instances, the TaqMan assays produced the same results as the classical PCR assays using either the *T. indica*-specific primers Tin3/Tin10 or the *T. walkeri*-specific primers Tin11/Tin10.

Figure 5A:
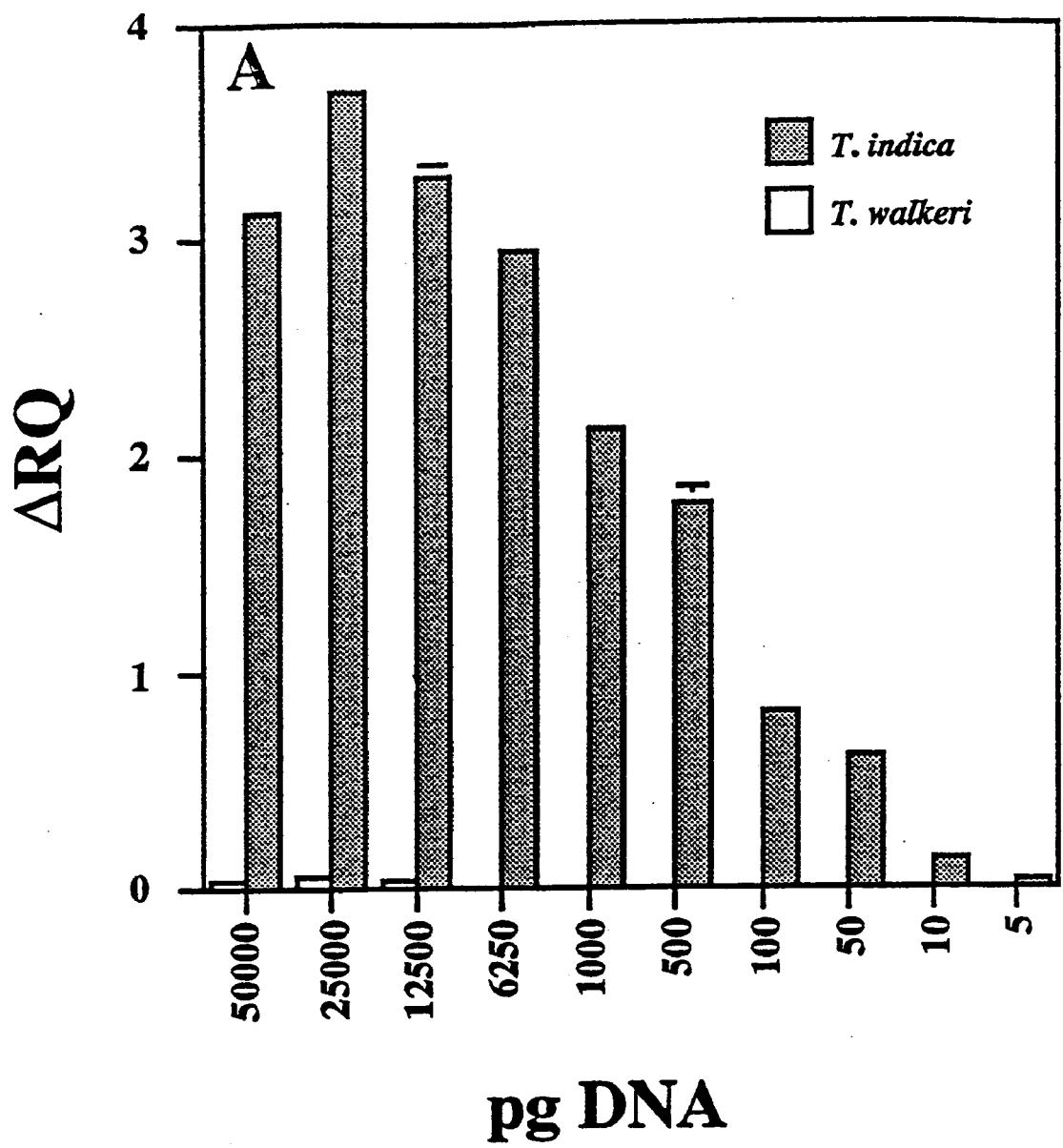
FIG. 5 shows the detection limits of *T. indica* and *T. walkeri* DNA by the TaqMan PCR assays using either the *T. indica*-specific flanking primers Tin3/Tin10 (A) or *T. walkeri*-specific flanking primers Tin11/Tin10 (B) after 34 cycles amplification. The ΔRQ values are the means of two independent experiments that had duplicate DNA samples. Error bars represent the standard errors of the means. Dilution series of template DNA were prepared from *T. indica* isolate Bpop and *T. walkeri* isolate YRG-001.
Figure 5B:
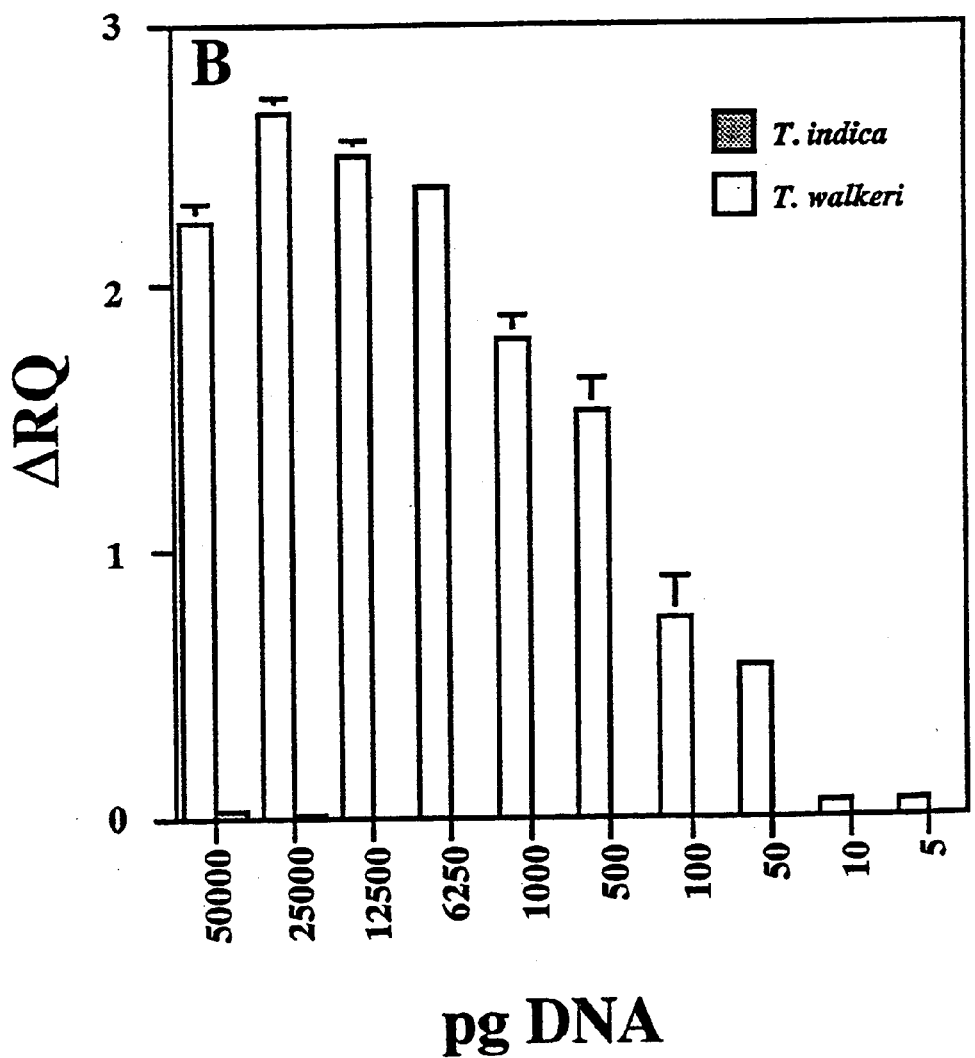

To determine the sensitivity limits of both *T. indica*- and the *T. walkeri*-specific 5' fluorogenic assays, dilutions of *T. indica* isolate Bpop and *T. walkeri* isolate YRG-001 purified total mycelial DNA were examined (FIG. 5). In both assays, 5 pg of total DNA produced detectable levels of fluorescence (0.06 and 0.04 ΔRQ values).

Figure 6A:
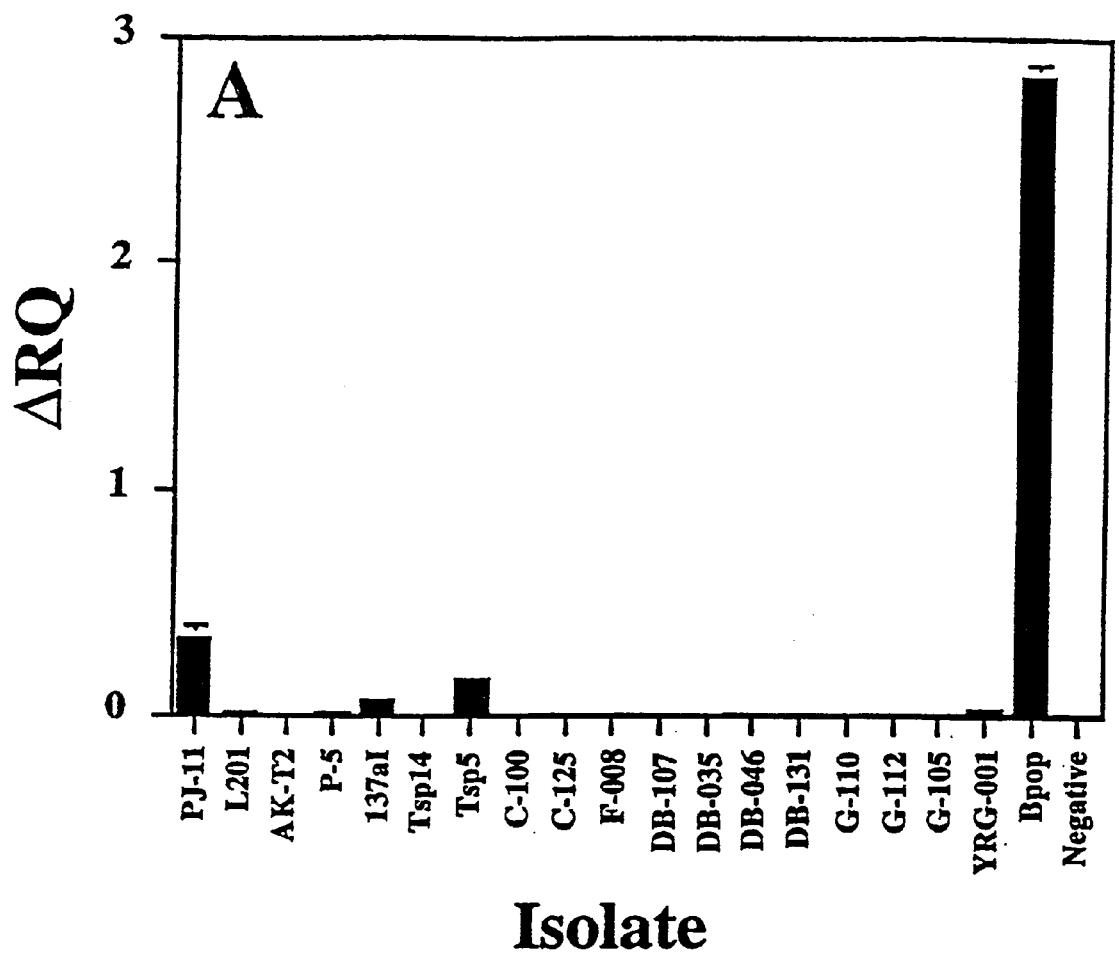
FIG. 6 shows TaqMan PCR amplification of mtDNA of Tilletia species using either the *T. indica*-specific flanking primers Tin3/Tin10 (A) or *T. walkeri*-specific flanking primers Tin11/Tin10 (B) after 34 cycles amplification. Duplicate DNA samples were analyzed for each isolate. *T. barclayana* is represented by isolates: PJ-11, L201, AK-T2, P-5, 137al, Tsp14, and Tsp5; *T. caries*, by isolates C-100 and C-125; *T. laevis*, by F-008; *T. controversa*, by DB-107, DB-035, DB046, and DB131; *T. fusca*, by G-110, G-112, and G-105; *T. walkeri*, by YRG-001; and *T. indica*, by Bpop.
Figure 6B:
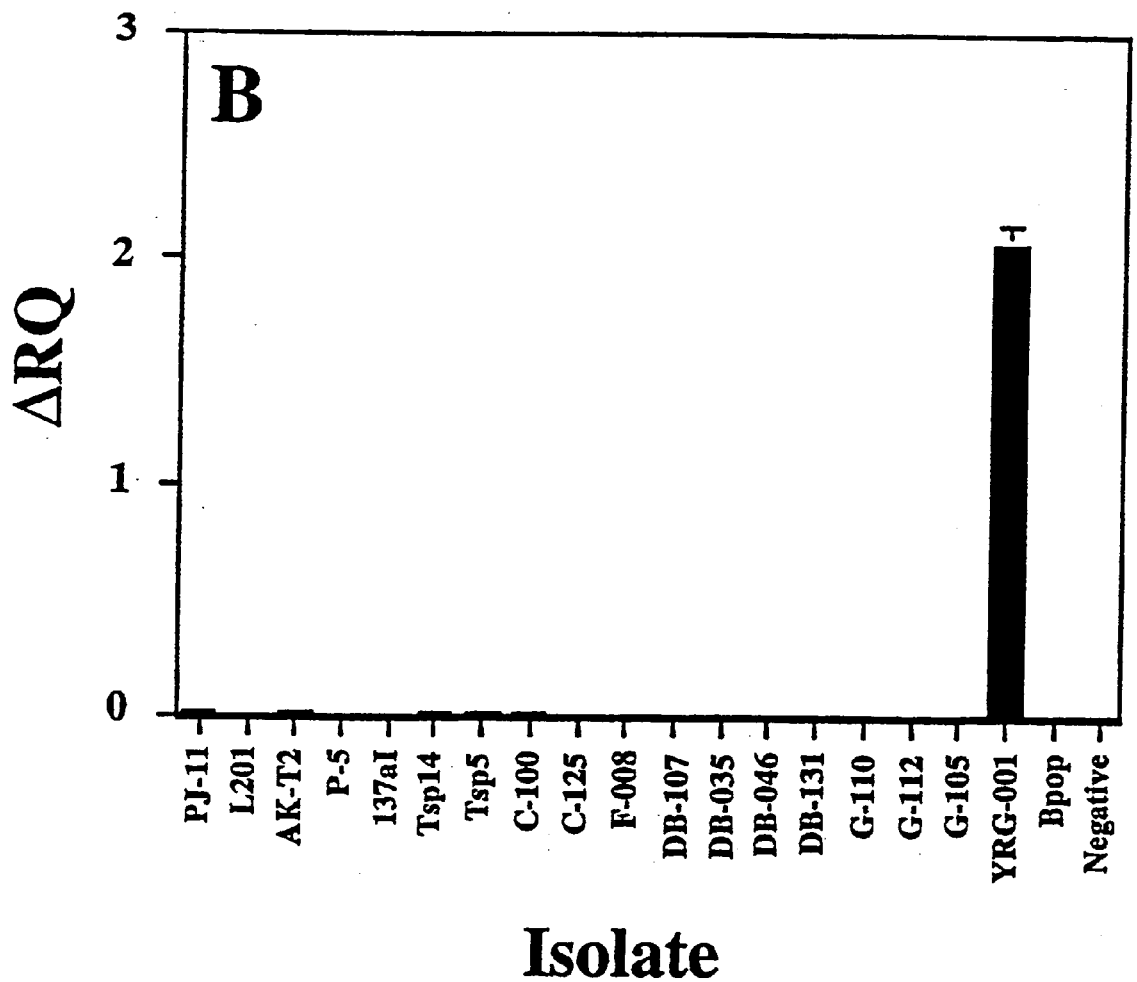

In order to verify the species specificity of both the *T. indica*- and the *T. walkeri*-specific 5' fluorogenic assays, purified total mycelial DNA of several different Tilletia species were evaluated (FIG. 6). None of the *T. barclayana, T. caries, T. laevis, T. controversa*, or *T. fusca* isolates showed any significant amplification in either the *T. indica*- or the *T. walkeri*-specific assay.

Example 7

Nucleotide Sequence Accession Numbers

The 2300 bp mtDNA sequence of *T. indica* isolates Yv3b, WL 1562, and Bpop and *T. walkeri* isolates 210G, TNRG-02, and YRG-001 have been deposited at GenBank and have been assigned the accession numbers AF218058, AF218059, AF218060, AF218061, AF218062, and AF218063, respectively.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An oligonucleotide primer consisting of the sequence 5'-CAATGTTGGCGTGGCG GCGC-3' (SEQ ID NO:1).

2. An oligonucleotide primer consisting of the sequence 5'-AGCTCCGCCTCA AGTTCCTC-3' (SEQ ID NO:2).

3. An oligonucleotide primer consisting of the sequence 5'-GGCACCAGAGTACAG CTGTCGTT-3' (SEQ ID NO:3).

4. An oligonucleotide primer consisting of the sequence 5'-GTCGGATTTGCG GACACTTTC-3' (SEQ ID NO:4).

5. An oligonucleotide primer consisting of the sequence 5'-GGCGGACTACCACTC GAGCT-3' (SEQ ID NO:5).

6. An oligonucleotide primer consisting of the sequence 5'-GACGTCGAGGCCGAC CGTAT-3' (SEQ ID NO:6).

7. An oligonucleotide primer consisting of the sequence 5'-CAACTCCAGTGATGG CTCCG-3' (SEQ ID NO:7).

8. A primer set comprising oligonucleotides consisting of the sequences 5'-GGCACC AGAGTACAGCTGTCGTT-3' (SEQ ID NO: 3) and 5'-GTCGGATTTGCGGACACTTTC-3' (SEQ ID NO:4).

9. A primer set comprising oligonucleotides consisting of the sequences 5'-CAATGT TGGCGTGGCGGCGC-3' (SEQ ID NO: 1) and 5'-GGCGGACTACCACTCGAGCT-3' (SEQ ID NO:5).

10. A primer set comprising oligonucleotides consisting of the sequences 5'-GACGTC GAGGCCGACCGTAT-3' (SEQ ID NO: 6) and 5'-GGCGGACTACCACTCGAGCT-3' (SEQ ID NO:5).

11. A primer set comprising oligonucleotides consisting of the sequences 5'-CAATGT TGGCGTGGCGGCGC-3' (SEQ ID NO:1) and 5'-CAACTCCAGTGATGGCTCCG-3' (SEQ ID NO:7).

12. A primer set comprising oligonucleotides consisting of the sequences 5'-CAATGT TGGCGTGGCGGCGC-3' (SEQ ID NO:1) and 5'-AGCTCCGCCTCAAGTTCCTC-3' (SEQ ID NO:2).

13. An oligonucleotide probe consisting of the sequence 5'-ATTCCCGGCTTC GGCGTCACT-3' (SEQ ID NO:11).

14. A method of detecting the presence of *T. indica* by polymerase chain reaction, said method comprising:
  a) providing the DNA of said *T. indica* or a test sample suspected of containing the DNA of said *T. indica*;
  b) amplifying a target sequence of DNA of said *T. indica* using at least one primer selected from the group consisting of the oligonucleotide 5'-GGCACC AGAGTACAGCTGTCGTT-3' (SEQ ID NO:3), the oligonucleotide 5'-GTCGGA TTTGCGGACACTTTC-3' (SEQ ID NO:4), the oligonucleotide 5'-CAATGTTGG CGTGGCGGCGC-3' (SEQ ID NO:1), the oligonucleotide 5'-GACGTCGAGGCC GACCGTAT-3' (SEQ ID NO:6); the oligonucleotide 5'-GGCGGACTACCACTC GAGCT-3' (SEQ ID NO:5), the oligonucleotide 5'-CAACTCCAGTGATGGCTCCG (SEQ ID NO:7), and the oligonucleotide 5'-AGCTCCGCCTCAAGTTCCTC-3' (SEQ ID NO:2); and
  c) detecting the presence of the amplification products of the target sequence of DNA as an indication of the presence of *T. indica*.

15. A method of detecting the presence of *T. indica* by polymerase chain reaction, said method comprising:
  a) providing the DNA of said *T. indica* or a test sample suspected of containing the DNA of said *T. indica*;

b) amplifying a target sequence of DNA of said *T. indica* using a primer set selected from the group consisting of (I) a primer set comprising oligonucleotides consisting of the sequence 5'-GGCACCAGAGTACAGCTGTCGTT-3' (SEQ ID NO:3) and the sequence 5'-GTCGGATTTGCGGACACTTTC-3' (SEQ ID NO:4), (ii) a primer set comprising oligonucleotides consisting of the sequence 5'-CAATGTTGGCGTGGCGGCGC-3' (SEQ ID NO:1) and the sequence 5'-GGCGGACTACCACTCGAGCT-3' (SEQ ID NO:5); (iii) a primer set comprising oligonucleotides consisting of the sequence 5'-GACGTCGAGGCCGACCGTAT-3' (SEQ ID NO:6) and the sequence 5'-GGCGGACTACCACTCGAGCT-3' (SEQ ID NO:5); (iv) a primer set comprising oligonucleotides consisting of the sequence 5'-CAATGTTGGCGTGGCGGCGC-3' (SEQ ID NO:1) and the sequence 5'-CAACTCCAGTGATGGCTCCG-3' (SEQ ID NO:7); (v) a primer set comprising oligonucleotides consisting of the sequence 5'-CAATGTTGGCGTGGCGGCGC-3' (SEQ ID NO:1) and the sequence 5'-AGCTCCGCCTCAAGTTCCTC-3' (SEQ ID NO:2); and c) detecting the presence of the amplification products of the target sequence of DNA as an indication of the presence of *T. indica*.

16. A kit for identifying *T. indica*, comprising at least one primer from the group consisting of the oligonucleotide 5'-GGCACCAGAGTACAGCTGTCGTT-3' (SEQ ID NO:3), the oligonucleotide 5'-GTCGGATTTGCGGACACTTTC-3' (SEQ ID NO:4), the oligonucleotide 5'-CAATGTTGGCGTGGCGGCGC-3' (SEQ ID NO:1), the oligonucleotide 5'-GACGTCGAGGCCGACCGTAT-3' (SEQ ID NO:6); the oligonucleotide 5'-GGCGGACTACCACTCGAGCT-3' (SEQ ID NO:5), the oligonucleotide 5'-CAACTCCAG TGATGGCTCCG (SEQ ID NO:7), and the oligonucleotide 5'-AGCTCCGCCTCAAGTTC CTC-3' (SEQ ID NO:2).

17. A kit for identifying *T. indica*, comprising a primer set selected from the group consisting of (a) the primer set comprising oligonucleotides consisting of the sequence 5'-GGCACCAGAGTACAGCTGTCGTT-3' (SEQ ID NO: 3) and the sequence 5'-GTC GGATTTGCGGACACTTTC-3' (SEQ ID NO:4), (b) a primer set comprising oligonucleotides consisting of the sequence 5'-CAATGTTGGCGTGGCGGCGC-3' (SEQ ID NO: 1) and the sequence 5'-GGCGGACTACCACTCGAGCT-3' (SEQ ID NO:5); (c) a primer set comprising oligonucleotides consisting of the sequence 5'-GACGTCGAG GCCGACCGTAT-3' (SEQ ID NO:6) and the sequence 5'-GGCGGACTACCACTCGA GCT-3' (SEQ ID NO:5); (d) a primer set comprising oligonucleotides consisting of the sequence 5'-CAATGTTGGCGTGGCGGCGC-3' (SEQ ID NO:1) and the sequence 5'-CAACTCCAGTGATGGCTCCG-3' (SEQ ID NO:7); and (e) a primer set comprising oligonucleotides consisting of the sequence 5'-CAATGTTGGCGTGGCGGCGC-3' (SEQ ID NO:1) and the sequence 5'-AGCTCCGCCTCAAGTTCCTC-3' (SEQ ID NO:2).

18. An oligonucleotide primer comprising a portion of SEQ ID NO:12, wherein said primer is twenty to twenty-four nucleotides in length, wherein the primer specifically hybridizes to a region of SEQ ID NO:12 such that the 3' terminal nucleotide is one of the 69 highlighted nucleotides identified in FIG. 1 as a mismatch between *T. indica* and *T. walkeri* and wherein the primer is capable of distinguishing *T. indica* from *T. walkeri* using PCR.

19. A method of detecting the presence of *T. indica* by polymerase chain reaction, said method comprising:

a) providing DNA of said *T. indica* or a test sample suspected of containing DNA of said *T. indica*;

b) amplifying a target sequence of DNA of said *T. indica* using at least one primer comprising a portion of SEQ ID NO:12, wherein said primer is twenty to twenty-four nucleotides in length, wherein the primer specifically hybridizes to a region of SEQ ID NO:12 such that the 3' terminal nucleotide is one of the 69 highlighted nucleotides identified in FIG. 1 as a mismatch between *T. indica* and *T. walkeri*, and wherein the primer is capable of distinguishing *T. indica* from *T. walkeri* using PCR; and c) detecting the presence of the amplification products of the target sequence of DNA as an indication of the presence of *T. indica*.

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Tilletia indica -continued

<400> SEQUENCE: 1
caatgttggc gtggcggcgc 20

<210> SEQ ID NO 2
<211> LENGTH: 20
<212> TYPE: DNA
<213> ORGANISM: Tilletia indica

<400> SEQUENCE: 2
agctccgcct caagttcctc 20

<210> SEQ ID NO 3
<211> LENGTH: 23
<212> TYPE: DNA
<213> ORGANISM: Tilletia indica

<400> SEQUENCE: 3
ggcaccagag tacagctgtc gtt 23

<210> SEQ ID NO 4
<211> LENGTH: 21
<212> TYPE: DNA
<213> ORGANISM: Tilletia indica

<400> SEQUENCE: 4
gtcggatttg cggacacttt c 21

<210> SEQ ID NO 5
<211> LENGTH: 20
<212> TYPE: DNA
<213> ORGANISM: Tilletia indica

<400> SEQUENCE: 5
ggcggactac cactcgagct 20

<210> SEQ ID NO 6
<211> LENGTH: 20
<212> TYPE: DNA
<213> ORGANISM: Tilletia indica

<400> SEQUENCE: 6
gacgtcgagg ccgaccgtat 20

<210> SEQ ID NO 7
<211> LENGTH: 20
<212> TYPE: DNA
<213> ORGANISM: Tilletia indica

<400> SEQUENCE: 7
caactccagt gatggctccg 20

<210> SEQ ID NO 8
<211> LENGTH: 20
<212> TYPE: DNA
<213> ORGANISM: Tilletia walkeri

<400> SEQUENCE: 8
taatgttggc gtggcggcat 20

<210> SEQ ID NO 9
<211> LENGTH: 20
<212> TYPE: DNA
<213> ORGANISM: Tilletia walkeri -continued

<400> SEQUENCE: 9
gtttgagcca cgctatgacc                                                    20

<210> SEQ ID NO 10
<211> LENGTH: 20
<212> TYPE: DNA
<213> ORGANISM: Tilletia walkeri

<400> SEQUENCE: 10
ggctcatcta cgcatacgtt 20

<210> SEQ ID NO 11
<211> LENGTH: 21
<212> TYPE: DNA
<213> ORGANISM: Tilletia indica

<400> SEQUENCE: 11
attcccggct tcggcgtcac t 21

<210> SEQ ID NO 12
<211> LENGTH: 2297
<212> TYPE: DNA
<213> ORGANISM: Tilletia indica

<400> SEQUENCE: 12
tgggctgagt ctgagatgca gagcctgcac tcccgaaaac gtcgacgagt ttggccgaac 60
gaagcgtgtg cgacacccga atccgtggaa gaacaacgct gagtgatcct agctgagcta 120
acgccgtcct ggattgtgca ctcttcgtca ccgccgttgc gcgcttagcg tgaatgctcc 180
tggaagccac agactatcag caaatgactc gaacagtttt tgtttcatca cacaagactc 240
acttgagcgg ctcgccttct tcttctgcaa tagtacctgt gggctcccct agggaagggc 300
tgccaggctc tccttggctg gcaccagagt acagctgtcg ttcttcctgc ctcgttttca 360
ccagagacat gactttcatg atggcctcga taccaacgtt ggtctcggcc agttccacgc 420
cgacatggac cgcttcgcgt tgcctgatct gcatcgacgg tcccaacacg aagttgaccc 480
gaaaggcgct gagccctggc agggacatga gccgtgccga gtcaggaatc gttttcctca 540
aagtcctgct agccgagccg gcttcgccgt aatagccctg tgcagaagtt gcccaaccag 600
aatcagaaga gaatgtggag tcggcaatag gctcgagcgc ccaatccgcc caccgatccg 660
tgaatccgct caaagtgagc gtgttcatgg tgtttagctt gctcgtgctg cttgacctct 720
tcagtgttcg cccacccaga tgcgcattcg acgagctcgc gacacttgca tcccgagaca 780
ttgtggtcgg agagaggaaa gtgtccgcaa atccgacttt cttcgccgat gatggcccac 840
tagcccgttc caccgcagat gatggaaagt cagattcagc ccgaacgatc cgtctgaccg 900
gggacatgct ttgaagcaat gttggcgtgg cggcgctgaa agatctgact tgagcgctag 960
gatcatgcgg caagtctgag gtatcgctgt ccatagactg cagtgacgcc gaagccggga 1020
atgagccggt cataggcgga gaggccagaa gctcggccag aggaacttga ggcggagctc 1080
tgctgttttt cgcctcgaac caccgagccg tggtggtctg gtatggagaa tagatactac 1140
catcggcaga acccgaagtc ggcagcggac tgagagtgaa agagccgctg cccattgcag 1200
catcgctcga gccactccgt tggtggccac gcgatcggtg gcgagccggc gccgaaaata 1260
ggggttgctt cgccgcttcg tgagtgccat actcttcatg gccctcacta tcggagccat 1320
cactggagtt gtcatggttg acacgagaat cagtcgcctg acgtcgaggc cgaccgtatc 1380

-continued

```
ggtcttgtcc tcttaccggt ctcaaaggtg accttgctgg ggactgcgtg ttttcatggc   1440
cgtccctcga agaatggagg ccgggtgaag gtatttggaa gaagctgtcc ctcttgtttg   1500
cactgcgtga aggttgccga aacgcgtgcg gttcggaaaa ggggtccggt tcgcctgtca   1560
cgaaaagcgc ttcgaagacc tgaattgact caaaagtcag cttcaagctt ccattcgcgg   1620
cggggacgcc agccattacg aaggcggtgg cacctctcgc cccagaaccg attcgatttg   1680
gcattgcagc gagcatttca gtgatgctat tttgaacgcc tggtattctc gaagctcgag   1740
tggtagtccg cccgtgaagc gtgtgagcca tgctatgact attcgctgcg gttctgttat   1800
tggaggaccg gccttcggac tgtatgggca tgtccttcat agctgaatcg aagggagat   1860 tttgtccgag tccattcgct gaagacgcg gtgtgacctg tgctcgtcca cgatgctcta   1920
catgtctggc agagacgact ttcatcgaat aacgagctcc catacgcccg acacggaaga   1980
cagtctcagc ttcttgtaca tagacttcga gccgatgaat ctccacttcg aaaagagagc   2040
ttacgaccgg gatcgccgat gctagaagga aaagaccgac cctcgtcccc ctcaagagcc   2100
aagactgtat ggtgggtatg acagcgtcgc ggacgtatgc gtagatgagc catccgacgt   2160
agagtgggac ggtgcgaaac gacgaggcgg acgttttgg aatcagagcg gaaaacggtc   2220
gccttggaag ttgcggccgc gctggaggtg cactagccac tgacccgctt cccaggctat   2280
gagacgcagg tattact                                                 2297
```

<210> SEQ ID NO 13
<211> LENGTH: 2300
<212> TYPE: DNA
<213> ORGANISM: Tilletia walkeri

<400> SEQUENCE: 13

```
tgggctgagt ctgagatgca gagcctgcac tcccgaaaac gtcgacgagt tttgccgaac     60
gaagcgtgtg cgacacccga atccgtggaa gaacaacgct gagtgatcct agctgagcta    120
acgccgtcct ggattgtgca ctcttcgtca ccgccgttgc gcgcttagcg tgaatgctcc    180
tggaagccac agactatcag caaatgactc gaacagcagt ttttgtttca tcacacaaga    240
ctcacttgag cggctcgcct tcttcttctg caatagtacc tgtgggctct cccagggaag    300
gactgccagc tctccttgg ctcgcaccag agtacagctt tcgtccttcc tgcctcgttt    360
tcaccagaga catgactttc atgatggcct ctataccgac gttggtctcg gccagttcca    420
cgccaacatg gaccgcttcg cgttgcctga tctgcatcga cggtcccaat acgaagttga    480
cccgaaaggc gctgagccct ggcagggaca tgagccgtgc cgagtcagga atcgtttcc    540 tcaaggtcct gctagccgag ccggcctcgc cgtaatagcc ctgtgcagag cttgcccaac    600
cagaatcaga agagaatgtg gagtcggcaa taggctcgag cgcccaatcc gcccaccgat    660
ccgtgaatcc gctcaaagtg agcgtgttca tggtgtttag cttactcgtg ctgcttgacc    720
tcttcagtgt ccgcccaccc agatgcgcat ttgacgagct cgcgacactc gcatcccgag    780
acattgtggt cggagagaga aaagtgtccg cgaatccaac tttcttcgct gatgatggcc    840
cactagcccg ttccaccgca gataatggaa agtcggattc agcccgaacg atccgtctga    900
ccggggacat gctttgaagt aatgttggcg tggcggcatt gaaagatctg acttgagcgc    960
taggatcatg cggcaagtct gaggcatcgc tgtccataga ctgcagtgac gccgaagccg   1020
ggaatgagcc ggtcaaaggc ggagaggcta aagctcggc cagaggaact tgaggcggag   1080
ctctgctgtt tttcgcttcg aaccaccgag ccgtggtggt ctggtatgga gaataaatac   1140
taccgtcggc agaacccgaa gtcggcagcg gactgagagt gaaagagccg ctgcccattg   1200
```

-continued

```
cagcatcgct cgagccactc cgttggtggc cacgcgatcg gtggcgaccc ggtgccgaaa  1260 atagggttg  cttcgccgct tcgtgagtgc catactcttc attgccctca ctatcggagc   1320
catcactgga gttctcatgg ttgacacgag gatcggtcgc ctgacgtcga ggccgaccat  1380
accggtcttg tcctcttacc ggtctcaaag gtgaccttgc tggggactgc gtgttttcat  1440
ggccgtccct cgaagaatgg aggccgggcg aaggtatttg gaagaagctg tccctcttgt  1500
ttgcactgcg tgaaggttgc cggaatgcgt gcggttcgga aaagggtcc  ggttcgcctg  1560 tcacgaaaag cgcttcgaag acctgtattg actcaaaagt cagctttaag cttccattcg  1620
cggcggggac gccagccatt acgaaggcgg tggcacctct cgcccagaa  ccgattcgat  1680 ttggcattgc agcgagcatt tcagtaatgc tattttgaac gcctggtatt ctcgaggctc  1740
gagtggtagt ccgcccgtga agtgtttgag ccacgctatg accattcgct gcggttctgt  1800
tgttggagga ccagccttcg gactgtatgg gcatgtcctt tatagctgga tcggaaggga  1860
gattttgtcc aagtccattt gctgaagacg gcggtgtgac ctgtgctcgt ccacgatgct  1920
ctacatgtct ggcagagacg actttcatcg aataacgagc tcccatacgc ccgacacgga  1980
agacagtctc agcttcttgt acatagactt cgagccgatg aatctccact tcgaaaagag  2040
agcttacgac cgggatcgcc gatgctagaa ggaaaagacc gaccctcgtc cccctcaaga  2100
gccaagactg gatcgtgggt atgacagcgt cgcgaacgta tgcgtagatg agccatccga  2160
catagagtgg gacggtgcga aacgacgagg cggaagtttt tggaatcaga gcggagaatg  2220
gtcgccttgg aagttgcggc cgcgctggag gtgcactagc cactgtcccg gtgcccaggc  2280
tatgagacgc aggtattact                                              2300
```